(12) United States Patent
Ashby et al.

(10) Patent No.: US 7,625,352 B1
(45) Date of Patent: Dec. 1, 2009

(54) DEPTH AND PUNCTURE CONTROL FOR SYSTEM FOR HEMOSTASIS OF BLOOD VESSEL

(75) Inventors: Mark Ashby, Laguna Niguel, CA (US); Andrew Cragg, Edina, MN (US); Luis Urquidi, Laguna Hills, CA (US); Eduardo Chi-Sing, Dana Point, CA (US); Eric Lee, Irvine, CA (US)

(73) Assignee: Sub-Q, Inc., San Clemente, CA (US)

( * ) Notice: Subject to any disclaimer, the term of this patent is extended or adjusted under 35 U.S.C. 154(b) by 458 days.

(21) Appl. No.: 09/621,670

(22) Filed: Jul. 24, 2000

Related U.S. Application Data

(60) Continuation-in-part of application No. 09/613,439, filed on Jul. 11, 2000, now Pat. No. 7,048,710, which is a division of application No. 09/071,284, filed on May 1, 1998, now Pat. No. 6,162,192.

(60) Provisional application No. 60/156,007, filed on Sep. 23, 1999.

(51) Int. Cl.
*A61F 13/20* (2006.01)
*A61F 13/36* (2006.01)

(52) U.S. Cl. .......................... 604/15; 604/60

(58) Field of Classification Search ............... 606/213, 606/191, 164, 215, 201; 604/15, 60
See application file for complete search history.

(56) References Cited

U.S. PATENT DOCUMENTS 581,235 A 4/1897 Kenyon
1,578,517 A 3/1926 Hein
2,086,580 A 6/1937 Shirley
2,370,319 A 2/1945 Lippinott
2,465,357 A 3/1949 Correll (Continued)

FOREIGN PATENT DOCUMENTS

EP 0032 826 1/1981

(Continued)

OTHER PUBLICATIONS

Vincent P. Chuang, M.D., et al., "Sheath Needle for Liver Biopsy in High-Risk Patients", *Radiology*, 166:261-262 (1988).

(Continued)

*Primary Examiner*—Ismael Izaguirre
(74) *Attorney, Agent, or Firm*—Crompton, Seager & Tufte LLC

(57) ABSTRACT

A depth and puncture control system for a blood vessel hemostasis system includes a blood vessel puncture control tip which, when positioned in the lumen of a blood vessel, can inhibit the flow of blood out of the puncture site. When used together with a pledget delivery cannula and a pledget pusher, the control tip and the delivery catheter can both inhibit blood loss out the puncture site and inhibit the introduction of pledget material and tissue fragments into the blood vessel. The system also includes a handle which releasably connects together the control tip, pusher, and delivery cannula to permit limited longitudinal motion between the control tip and the delivery cannula, and between the pusher and the delivery cannula.

37 Claims, 15 Drawing Sheets

U.S. PATENT DOCUMENTS

| | | | |
|---|---|---|---|
| 2,492,458 A | 12/1949 | Bering, Jr. | |
| 2,507,244 A | 5/1950 | Correll | |
| 2,558,395 A | 6/1951 | Studer | |
| 2,597,011 A | 5/1952 | MacMasters et al. | |
| 2,680,442 A | 6/1954 | Linzmayer | |
| 2,761,446 A | 9/1956 | Reed | |
| 2,814,294 A | 11/1957 | Figge | |
| 2,824,092 A | 2/1958 | Thompson | |
| 2,828,744 A * | 4/1958 | Hirsch et al. | 604/165.01 |
| 2,874,776 A | 2/1959 | Hooe | |
| 2,899,362 A | 8/1959 | Sieger, Jr. et al. | |
| 3,157,524 A | 11/1964 | Artandi | |
| 3,358,689 A | 12/1967 | Higgins | |
| 3,411,505 A | 11/1968 | Nobis | |
| 3,724,465 A | 4/1973 | Duchane | |
| 3,736,939 A | 6/1973 | Taylor | |
| 4,000,741 A | 1/1977 | Binard et al. | |
| 4,098,728 A | 7/1978 | Rosenblatt | |
| 4,211,323 A | 7/1980 | Olsen | |
| 4,218,155 A | 8/1980 | Weidner | |
| 4,219,026 A | 8/1980 | Layton | |
| 4,224,945 A | 9/1980 | Cohen | |
| 4,238,480 A | 12/1980 | Sawyer | |
| 4,292,972 A | 10/1981 | Paweichak | |
| 4,323,072 A | 4/1982 | Rosenbluth et al. | |
| 4,340,066 A | 7/1982 | Shah | |
| 4,390,018 A | 6/1983 | Zukowski | |
| 4,404,970 A | 9/1983 | Sawyer | |
| 4,405,314 A | 9/1983 | Cope | |
| 4,515,637 A | 5/1985 | Cioca | |
| 4,573,576 A | 3/1986 | Krol | |
| 4,587,969 A | 5/1986 | Gillis | |
| 4,588,395 A | 5/1986 | Lemelson | |
| 4,619,261 A | 10/1986 | Guerrero | |
| 4,619,913 A | 10/1986 | Luck et al. | |
| 4,644,649 A | 2/1987 | Seaman et al. | |
| 4,645,488 A | 2/1987 | Matukas | |
| 4,699,616 A | 10/1987 | Norwak | |
| 4,708,718 A | 11/1987 | Daniels | |
| 4,744,364 A | 5/1988 | Kensey | |
| 4,790,819 A | 12/1988 | Li et al. | |
| 4,829,994 A | 5/1989 | Kurth | |
| 4,832,688 A | 5/1989 | Sagae et al. | |
| 4,839,204 A | 6/1989 | Yoshino et al. | |
| 4,850,960 A | 7/1989 | Grayzel | |
| 4,852,568 A | 8/1989 | Kensey | |
| 4,869,143 A | 9/1989 | Merrick | |
| 4,890,612 A | 1/1990 | Kensey | |
| 4,900,303 A | 2/1990 | Lemelson | |
| 4,929,246 A | 5/1990 | Sinofsky | |
| 4,936,835 A | 6/1990 | Haaga | |
| 4,950,234 A | 8/1990 | Fujioka et al. | |
| 5,007,895 A | 4/1991 | Burnett | |
| 5,021,059 A | 6/1991 | Kensey et al. | |
| 5,049,138 A | 9/1991 | Chevalier et al. | |
| 5,053,046 A | 10/1991 | Janese | |
| 5,061,274 A | 10/1991 | Kensey | |
| 5,080,655 A | 1/1992 | Haaga | |
| 5,108,421 A | 4/1992 | Fowler | |
| 5,129,889 A | 7/1992 | Hahn | |
| 5,163,904 A | 11/1992 | Lampropoulos et al. | |
| 5,167,624 A | 12/1992 | Butler et al. | |
| 5,192,290 A | 3/1993 | Hilal | |
| 5,192,300 A | 3/1993 | Fowler | |
| 5,192,301 A | 3/1993 | Kamiya et al. | |
| 5,195,988 A | 3/1993 | Haaga | |
| 5,219,899 A | 6/1993 | Panster et al. | |
| 5,220,926 A | 6/1993 | Jones | |
| 5,221,259 A | 6/1993 | Weldon et al. | |
| 5,232,453 A | 8/1993 | Plass et al. | |
| 5,242,683 A | 9/1993 | Klaveness | |
| 5,254,105 A | 10/1993 | Haaga | |
| 5,275,616 A | 1/1994 | Fowler | |
| 5,282,827 A | 2/1994 | Kensey | |
| 5,292,309 A * | 3/1994 | Van Tassel et al. | 604/117 |
| 5,310,407 A | 5/1994 | Casale | |
| 5,320,639 A | 6/1994 | Rudnick | |
| 5,322,515 A | 6/1994 | Karas et al. | |
| 5,325,857 A | 7/1994 | Nabai et al. | |
| 5,334,216 A | 8/1994 | Vidal et al. | |
| 5,342,388 A | 8/1994 | Toller | |
| 5,350,399 A | 9/1994 | Erlebacher et al. | |
| 5,352,211 A | 10/1994 | Merskelly | |
| 5,366,480 A | 11/1994 | Corriveau et al. | |
| 5,370,656 A | 12/1994 | Shevel | |
| 5,383,896 A | 1/1995 | Gershony et al. | |
| 5,383,899 A | 1/1995 | Hammerslag | |
| 5,385,550 A | 1/1995 | Su et al. | |
| 5,388,588 A | 2/1995 | Nabai et al. | |
| 5,391,183 A | 2/1995 | Janzen et al. | |
| 5,399,361 A | 3/1995 | Song et al. | |
| 5,417,699 A | 5/1995 | Klein | |
| 5,419,765 A | 5/1995 | Weldon et al. | |
| 5,431,639 A | 7/1995 | Shaw | |
| 5,437,292 A | 8/1995 | Kipshidze | |
| 5,437,631 A * | 8/1995 | Janzen | 604/506 |
| 5,443,481 A | 8/1995 | Lee | |
| 5,447,502 A | 9/1995 | Haaga | |
| 5,458,570 A | 10/1995 | May, Jr. | |
| 5,462,194 A | 10/1995 | Barawell | |
| 5,467,780 A | 11/1995 | Nabai et al. | |
| 5,478,352 A | 12/1995 | Fowler | |
| 5,479,936 A | 1/1996 | Nabai et al. | |
| 5,486,195 A | 1/1996 | Myers et al. | |
| 5,490,736 A | 2/1996 | Haber | |
| 5,507,279 A | 4/1996 | Fortune et al. | |
| 5,522,840 A | 6/1996 | Krajicek | |
| 5,522,850 A | 6/1996 | Yomtov et al. | |
| 5,526,822 A | 6/1996 | Burbank et al. | |
| 5,527,332 A | 6/1996 | Clement | |
| 5,529,577 A | 6/1996 | Hammerslag | |
| 5,540,715 A | 7/1996 | Katsaros et al. | |
| 5,542,914 A | 8/1996 | Van Iten | |
| 5,545,175 A | 8/1996 | Abidin et al. | |
| 5,545,178 A | 8/1996 | Kensey et al. | |
| 5,558,853 A | 9/1996 | Quay | |
| 5,571,168 A | 11/1996 | Toro | |
| 5,591,204 A | 1/1997 | Janzen et al. | |
| 5,591,205 A | 1/1997 | Fowler | |
| 5,601,601 A | 2/1997 | Tal et al. | |
| 5,601,602 A | 2/1997 | Fowler | |
| 5,601,603 A | 2/1997 | Illi | |
| 5,620,461 A | 4/1997 | Muijs Van De Moer et al. | |
| 5,645,566 A * | 7/1997 | Brenneman et al. | |
| 5,649,547 A | 7/1997 | Ritchart et al. | |
| 5,653,730 A | 8/1997 | Hammerslag | |
| 5,665,107 A | 9/1997 | Hammerslag | |
| 5,674,346 A | 10/1997 | Kundel | |
| 5,676,689 A | 10/1997 | Kensey et al. | |
| 5,681,279 A | 10/1997 | Roper et al. | |
| 5,707,393 A | 1/1998 | Kensey et al. | |
| 5,716,375 A | 2/1998 | Fowler | |
| 5,725,498 A | 3/1998 | Janzen et al. | |
| 5,728,132 A | 3/1998 | Van Tassel et al. | |
| 5,741,223 A | 4/1998 | Janzen et al. | |
| 5,769,086 A | 6/1998 | Ritchart et al. | |
| 5,775,333 A | 7/1998 | Burbank et al. | |
| 5,782,861 A | 7/1998 | Cragg et al. | |
| 5,792,152 A * | 8/1998 | Klein et al. | 606/144 |
| 5,800,389 A | 9/1998 | Burney et al. | |
| 5,810,806 A | 9/1998 | Ritchart et al. | |
| 5,830,130 A | 11/1998 | Janzen et al. | |
| 5,858,008 A | 1/1999 | Capaccio | |
| 5,868,762 A | 2/1999 | Cragg et al. | |

| | | | |
|---|---|---|---|
| 5,902,310 A | 5/1999 | Foerster et al. | |
| 5,931,165 A | 8/1999 | Reich et al. | |
| 5,984,950 A | 11/1999 | Cragg et al. | |
| 6,007,563 A | 12/1999 | Nash et al. | |
| 6,027,471 A | 2/2000 | Fallon et al. | |
| 6,027,482 A | 2/2000 | Imbert | |
| 6,033,427 A | 3/2000 | Lee | |
| 6,056,768 A | 5/2000 | Cates et al. | |
| 6,066,325 A | 5/2000 | Wallace et al. | |
| 6,071,300 A | 6/2000 | Brenneman et al. | |
| 6,071,301 A | 6/2000 | Cragg et al. | |
| 6,086,607 A | 7/2000 | Cragg et al. | |
| 6,090,130 A | 7/2000 | Nash et al. | |
| 6,126,675 A | 10/2000 | Shchervinsky et al. | |
| 6,161,034 A | 12/2000 | Burbank et al. | |
| 6,162,192 A * | 12/2000 | Cragg et al. | 604/15 |
| 6,183,497 B1 | 2/2001 | Sing et al. | |
| 6,200,328 B1 | 3/2001 | Cragg et al. | |
| 6,315,753 B1 * | 11/2001 | Cragg et al. | 604/15 |
| 6,371,974 B1 | 4/2002 | Brenneman et al. | |
| 6,440,151 B1 | 8/2002 | Cragg et al. | |
| 6,440,153 B2 | 8/2002 | Cragg et al. | |
| 6,503,222 B2 | 1/2003 | Lo | |
| 6,527,734 B2 | 3/2003 | Cragg et al. | |
| 6,540,735 B1 | 4/2003 | Ashby et al. | |
| 6,544,236 B1 | 4/2003 | Cragg et al. | |
| 6,610,026 B2 | 8/2003 | Cragg et al. | |
| 6,818,008 B1 * | 11/2004 | Cates et al. | 606/213 |
| 2002/0002889 A1 | 1/2002 | Ashby et al. | |
| 2002/0016612 A1 | 2/2002 | Ashby et al. | |
| 2002/0038133 A1 | 3/2002 | Sing et al. | |
| 2002/0042378 A1 | 4/2002 | Reich et al. | |
| 2002/0062104 A1 | 5/2002 | Ashby et al. | |
| 2002/0156495 A1 | 10/2002 | Brenneman et al. | |
| 2003/0028140 A1 | 2/2003 | Greff et al. | |
| 2003/0088269 A1 | 5/2003 | Ashby | |
| 2003/0088271 A1 | 5/2003 | Cragg et al. | |
| 2003/0120258 A1 | 6/2003 | Ashby et al. | |
| 2003/0135237 A1 | 7/2003 | Cragg et al. | |
| 2004/0019328 A1 | 1/2004 | Sing et al. | |
| 2004/0019330 A1 | 1/2004 | Ashby | |

FOREIGN PATENT DOCUMENTS

| | | |
|---|---|---|
| EP | 032826 A2 | 7/1981 |
| EP | 476178 A1 | 3/1992 |
| EP | 482350 A2 | 4/1992 |
| EP | 0 557 963 | 2/1993 |
| EP | 0 637 431 | 7/1994 |
| EP | 0637432 B1 | 7/1994 |
| FR | 2 641 692 | 7/1990 |
| GB | 1509023 | 4/1978 |
| GB | 1569660 | 6/1980 |
| SU | 782814 | 11/1980 |
| SU | 1088709 A | 4/1984 |
| WO | WO91/12847 | 9/1991 |
| WO | WO94/02072 | 7/1993 |
| WO | WO94/28800 | 12/1994 |
| WO | WO95/28124 | 10/1995 |
| WO | WO95/32669 | 12/1995 |
| WO | WO95/32671 | 12/1995 |
| WO | WO96/08208 | 3/1996 |
| WO | WO96/242290 | 8/1996 |
| WO | WO97/07934 | 3/1997 |
| WO | WO98/06346 | 2/1998 |
| WO | WO 98/40016 | 9/1998 |
| WO | WO 99/56692 | 11/1999 |
| WO | WO99/666834 | 12/1999 |

OTHER PUBLICATIONS

Marc Zins, M.D., et al., "US-guided Percutaneous Liver Biopsy with Plugging of the Needle Track: A Prospective Study in 72 High-Risk Patients", *Radiology*, 184(3):841-843 (1992).

Tony P. Smith, M.D., et al., "Percutaneous Transhepatic Liver Biopsy with Tract Embolization", *Radiology*, 198:769-774 (1996).

S.A. Riley, et al., "Percutaneous Liver Biopsy with Plugging of Needle Track: A Safe Method for Use in Patients with Impaired Coagulation", *The Lancet*, p. 436 (1984).

David J. Allison, M.D., et al., "Percutaneous Liver Biopsy and Track Embolization with Steel Coils", *Radiology*, 169(1):261-263 (1988).

Fandrich, C., et al. Small Gauge Gelfoam Plug Liver Biopsy in High Risk Patients:, Australian Rdiology, vol. 40, pp. 230-234 (1996).

Journal of Interventional Cardiology vol. 5 No. 2 Jun. 1992.

J. Bryne Review Article; Endovascular treatments for intracranial anuerysms, 1996 The British Journal of Rdiology 68, 891-899.

John T. Correll et al. A New Physiologically Asorbable sponge.

John T. Correll, et al. A new physiologically absorbable sponge.

Kassell et al. Size of intracranial aneursysm; vol. 12, No. 3, 1983.

Szikora, et al. Combined use of stents and cells to treat experimental wide-necked carotid aneurysms: Prliminary ruesults; AJNR AM newroradio15: 1091-1102, Jun. 1994.

Szikora, et al. Endovascular treatment of experimental anuerysms with liquid polymers: vol. 38, No. 2, Feb. 1996.

Yoshimoto, et al. Cerebral aneurysms unrelated to arterial bifurcations; Acta Neurochir (Wien) (96) 138: 958-964.

Schievink, et al. The new england journal of medicine; review articles; intracanial aneurysms; Jan. 2, 1997.

Turjman, et al. Combined stent implantation & enosacular coil placement for treatment of experimental wide-necked aneurysms: AJNR AM J. Neuroradiol 15: 1087-1090 Jun. 1994.

Berman, et al "Guided Direct Antegrade Puncture of the Superficial Femoral Artery" AJR 147:632-634, Sep. 1986 0361-803X86/1473-0632 © American Roentgen Ray Society.

Berman et al "Modification of the Cope Drainage Catheter to Facilitate Placement" AJR 146:169-170, Jan. 1986 0361-803X-86/1461-0169 © American Ray Society.

Correll, John T. et al. Biologic investigations of new absorbable sponge; p. 585.

Di Seni, Ricardo, et al, "Part 1, Embolotherapy: Agents, Equipment, and Techniques," Vascular Embolotherapy, vol. 4, pp. 29 & 33.

Saddekni, MD et al "Antegrade Catheterization of the Superficial Femoral Artery" Radiology 1985 157:561-532.

Vogelzang "A Modified Cope Introducing Dilator to Allow Straight Guide Wire Introduction" AJR 146:381-382 Feb. 1986 0361-803X/86/1462-0381 © American Roentgen Ray Society.

Our Pending Applications.

Ashby, Mark et al; U.S. Appl. No. 10/287,922, filed Nov. 4, 2002; entitled: Apparatus And Method For Inhibiting Blood Loss.

Ashby, Mark et al; U.S. Appl. No. 10/069,107, filed Dec. 16, 2002; entitled: Device And Method For Determining A Depth Of An Incision.

Ashby, Mark et al; U.S. Appl. No. 10/278,710, filed Oct. 22, 2002; entitled: System and Method for Facilitating Hemostasis of Blood Vessel Punctures With Absorbable Sponge.

Ashby, Mark et al; U.S. Appl No. 10/334,770, filed Dec. 31, 2002; entitled: Improved System and Method for Facilitating Hemostasis with Absorbable Sponge.

Ashby, Mark et al; U.S. Appl. No. 10/421,680, filed Apr. 22, 2003; entitled: Puncture Closure System With Pin And Pull Technique.

Ashby, Mark et al; U.S. Appl. No. 10/462,065, filed Jun. 12, 2003; entitled: Enhanced Bleed Back System.

Ashby, Mark et al, U.S. Appl. No. 10/462,064, filed Jun. 12, 2003; entitled: Release Mechanism.

Ashby, Mark et al; U.S. Appl. No. 10/461,587, filed Jun. 12, 2003; entitled: Dissolvable Closure Device.

Ashby, Mark et al; U.S. Appl. No. 10/461,035, filed Jun. 13, 2003; entitled: System And Method For Delivering Hemostasis Promoting Material To A Blood Vessel Puncture Site Using a Cannula.

Ashby, Mark et al; U.S. Appl. No. 10/461,006, filed Jun. 13, 2003; entitled: System and Method for Delivering Hemostasis Promoting Material to a Blood Vessel Puncture with a Staging Tube.

Ashby, Mark et al; U.S. Appl. No. 10/460,859, filed Jun. 12, 2003; entitled: Hemostatic Device Including a Capsule.

Ashby, Mark et al; U.S. Appl. No. 10/732,441, filed Dec. 9, 2003; entitled: Pledget-Handling System and Method for Delivering Hemostasis Promoting Material to a Blood Vessel Puncture Site By Fluid Pressure.

Ashby, Mark et al; U.S. Appl No. 10/754,824, filed Jan. 9, 2004; entitled: Sheath-Mounted Arterial Plug Delivery Device.

Supplementary European Search Report EP 00 96 6874; report dated Jul. 1, 2008.

* cited by examiner

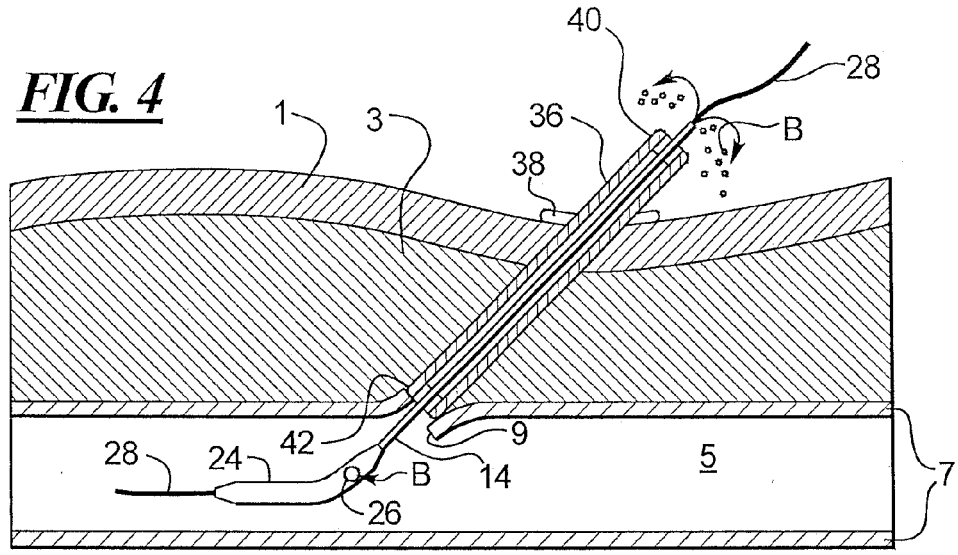
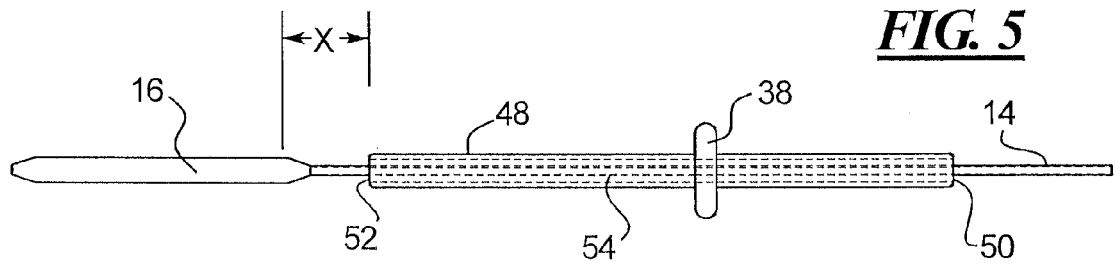
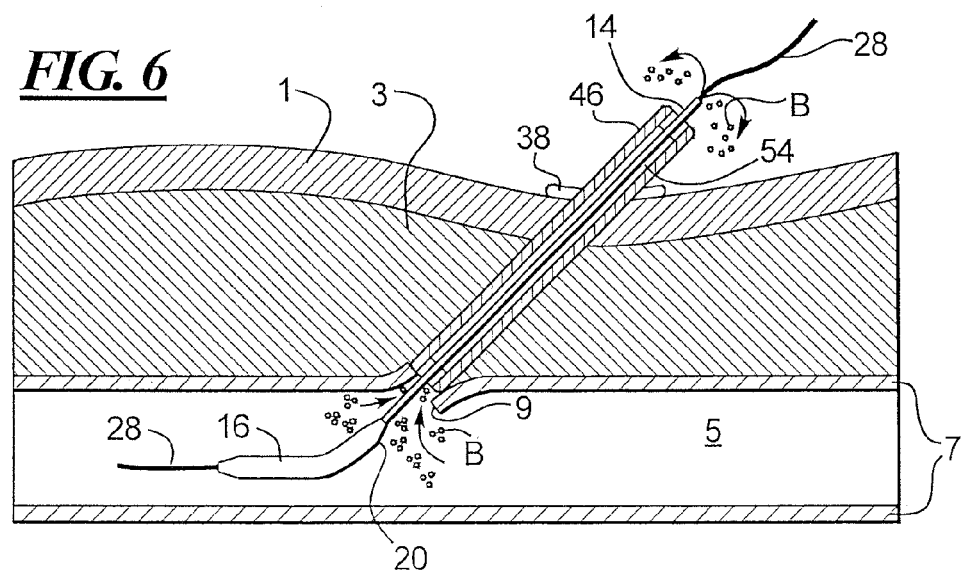

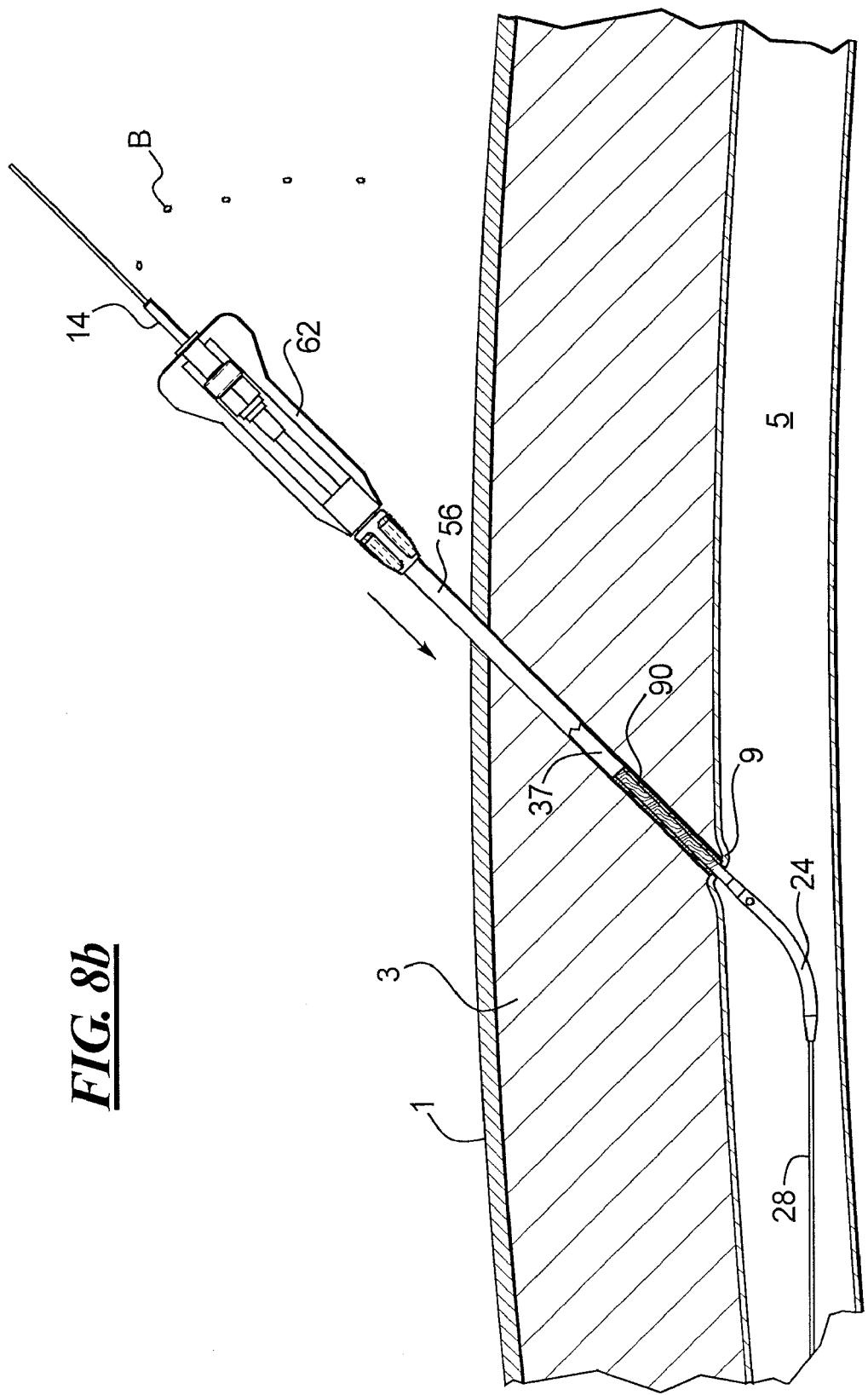

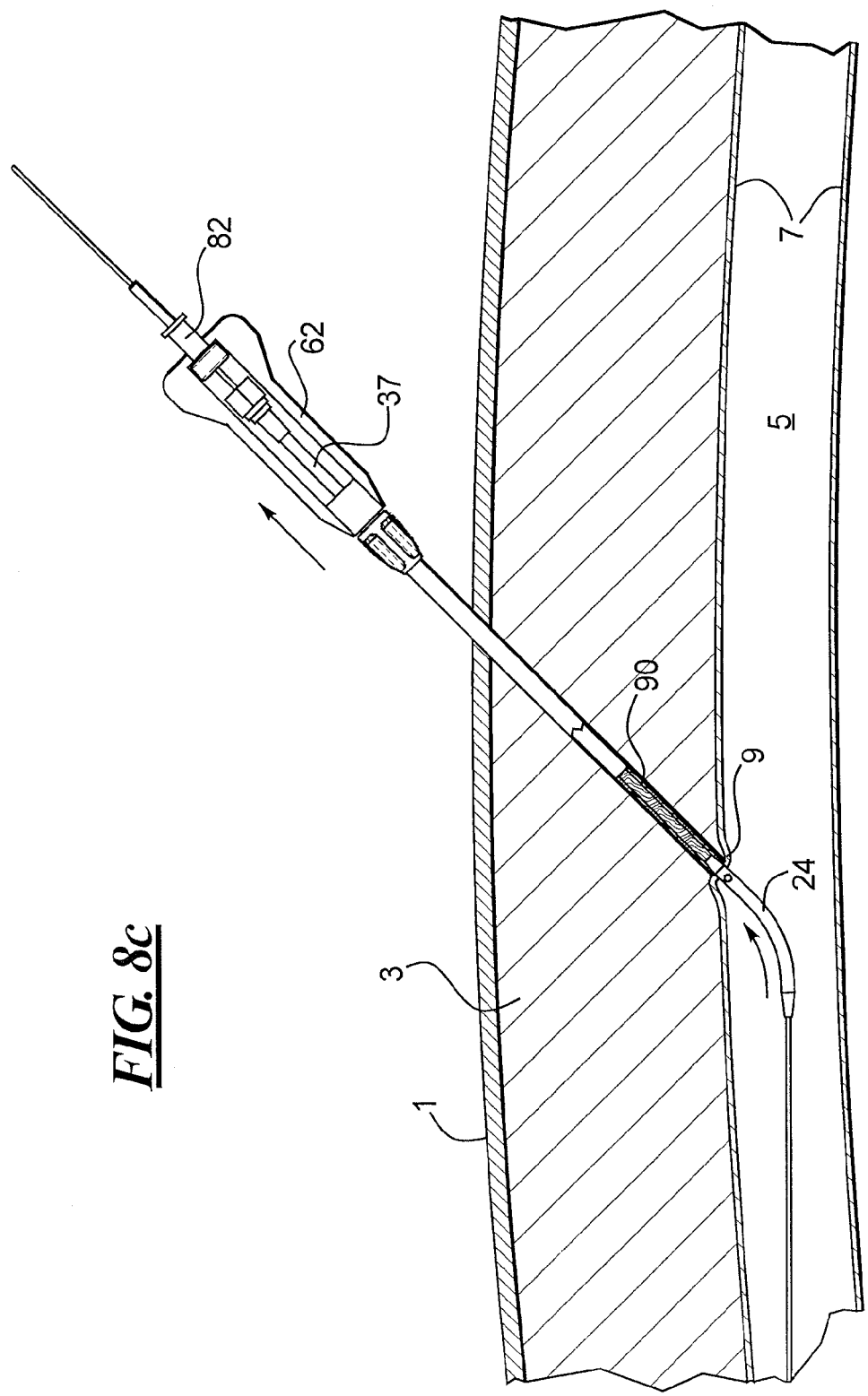

DEPTH AND PUNCTURE CONTROL FOR SYSTEM FOR HEMOSTASIS OF BLOOD VESSEL

CROSS-REFERENCE TO RELATED APPLICATIONS

This application is a continuation-in-part and claims priority to U.S. patent application Ser. No. 09/613,439, entitled "System and Method for Facilitating Hemostasis of Blood Vessel Punctures with Absorbable Sponge" by inventors Andrew H. Cragg, Rodney Brenneman, and Mark Ashby, filed on Jul. 11, 2000 now U.S. Pat. No. 7,048,710, which is a divisional of U.S. patent application Ser. No. 09/071,284 filed May 1, 1998, by inventors Andrew H. Cragg, Rodney Brenneman, and Mark Ashby, now issued as U.S. Pat. No. 6,162,192. This application further claims the benefit of U.S. Provisional Application No. 60/156,007, filed Sep. 23, 1999.

BACKGROUND OF THE INVENTION

1. Field of the Invention

The invention relates to closure systems and methods for blood vessel puncture sites.

2. Brief Description of the Related Art

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface and may be unsuitable for patients with substantial amounts of subcutaneous adipose tissue since the skin surface may be a considerable distance from the vascular puncture site.

More recently, devices have been proposed to promote hemostasis directly at a site of a vascular puncture. One class of such puncture sealing devices features an intraluminal anchor which is placed within the blood vessel and seals against an inside surface of the vessel puncture. The intraluminal plug may be used in combination with a sealing material positioned on the outside of the blood vessel, such as collagen. Sealing devices of this type are disclosed in U.S. Pat. Nos. 4,852,568; 4,890,612; 5,021,059; and 5,061,274.

Another approach to subcutaneous blood vessel puncture closure involves the delivery of non-absorbable tissue adhesives, such cyanoacrylate, to the perforation site. Such a system is disclosed in U.S. Pat. No. 5,383,899.

The application of an absorbable material such as collagen or a non-absorbable tissue adhesive at the puncture site has several drawbacks including: 1) possible injection of the material into the blood vessel causing thrombosis; 2) a lack of pressure directly on the blood vessel puncture which may allow blood to escape beneath the material plug into the surrounding tissue; and 3) the inability to accurately place the absorbable material plug directly over the puncture site.

The use of an anchor and plug system addresses these problems to some extent but provides other problems including: 1) complex and difficult application; 2) partial occlusion of the blood vessel by the anchor when placed properly; and 3) complete blockage of the blood vessel or a branch of the blood vessel by the anchor if placed improperly. Another problem with the anchor and plug system involves reaccess. Reaccess of a particular blood vessel site sealed with an anchor and plug system is not possible until the anchor has been completely absorbed because the anchor could be dislodged into the blood stream by an attempt to reaccess.

Such puncture sealing devices are generally used in conjunction with a cannula or arterial dilator which dilates an access tract in the tissue before inserting the sealing device for placing the intraluminal or sealing plug. By using the cannula to dilate the access tract, the sealing device can be easily advanced into the tissue toward the vascular puncture. However, a conventional cannula has either a constant diameter lumen which is sized to closely accommodate a guidewire, or the diameter of the lumen narrows at the distal end. When these conventional cannulas are advanced into the access tract, the cannulas often encounter scar or muscular tissue that requires substantial force to advance the cannula through these layers. In prior conventional cannulae, a cannula which has a constant diameter lumen may enter the vascular puncture while being advanced into the access tract, or the cannula will bounce against a wall of the blood vessel rather than accurately locate the blood vessel wall. Accordingly, the sealing plug may not be accurately placed over the puncture site.

Accordingly, it would be desirable to provide a system for accurately locating the blood vessel wall for properly placing a hemostasis plug over a puncture site.

SUMMARY OF THE INVENTION

According to one aspect of the present invention, an apparatus useful for inhibiting blood loss out a puncture site in a blood vessel wall and for indicating the location of a blood vessel comprises a vent tube including a tubular shaft having a proximal end, a distal end, and a lumen extending longitudinally between the proximal end and the distal end, and a control head on the distal end of the vent tube shaft, the control head including a proximal end portion, a distal end portion having a distal port, and a central portion between the proximal end portion and the distal end portion, the control head including a lumen extending from the distal port to the vent tube shaft lumen.

According to another aspect of the present invention, a pledget delivery and blood vessel puncture site control system comprises a control tip including a vent tube having a tubular shaft with a proximal end, a distal end, and a lumen extending longitudinally between the proximal end and the distal end, and a control head on the distal end of the vent tube shaft, the control head including an externally tapered proximal end portion, a distal end portion having a distal port, and a central portion between the proximal end portion and the distal end portion, the control head including a lumen extending from the distal port to the vent tube shaft lumen, a pledget pusher positioned around the vent tube shaft, the pledget pusher including a tubular shaft having a proximal end, a distal end, and a lumen extending longitudinally between the pledget pusher proximal end and the pledget pusher distal end, the inner diameter of the pledget pusher lumen being larger than the outer diameter of the vent tube, a delivery cannula positioned around the pledget pusher, the delivery cannula including a tubular shaft having a proximal end, a distal end, and a lumen extending longitudinally between the delivery cannula proximal end and the delivery cannula distal end, the inner diameter of the delivery cannula lumen being larger than the outer diameter of the pledget pusher, the control head extending distally from the delivery cannula distal end, the delivery cannula distal end extending distally of the pledget pusher distal end.

According to another aspect of the present invention, a method of positioning a pledget adjacent to the exterior surface of a blood vessel puncture site in a patient comprises the steps of advancing a control head of a control tip through the puncture site and at least partially into the blood vessel, the control tip including a proximal portion extending out of the puncture site and out of the patient, advancing an assembly over the control tip proximal portion and adjacent to an exterior surface of the blood vessel, the assembly including a delivery cannula having a lumen, a pledget pusher in the delivery cannula, and a pledget in the delivery cannula, proximally retracting the control head to engage the pledget, and expelling the pledget from the delivery cannula.

According to yet another aspect of the present invention, a method of measuring the distance between an epidermal outer surface and the outer surface of a blood vessel, the blood vessel having a puncture therethrough at a puncture site, comprises the steps of advancing a control tip through subcutaneous tissue and into the blood vessel through the puncture, advancing a tubular shaft over the control tip until a distal end of the tubular shaft engages the outer surface of the blood vessel, and positioning a marker along the tubular shaft against the epidermal outer surface.

According to yet another aspect of the present invention, a method of at least partially controlling blood flow through a puncture site in a blood vessel wall comprises the steps of inserting a control tip through the vessel wall at the puncture site and at least partially into the blood vessel, and positioning a pledget adjacent to an outer surface of the blood vessel wall at the puncture site with the control tip still at least part in the vessel puncture site.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which:

FIG. 4 schematically illustrates portions of the first embodiment, illustrated in FIG. 3a, positioned in a blood vessel of a patient;

FIG. 5 illustrates a side elevational view of portions of a second embodiment of a system in accordance with the present invention;

FIG. 6 schematically illustrates portions of the second embodiment, illustrated in FIG. 5, positioned in a blood vessel of a patient;

FIGS. 8a–8f illustrate steps of an exemplary method in accordance with the present invention;

DESCRIPTION OF PREFERRED EMBODIMENTS

Figure 1A:
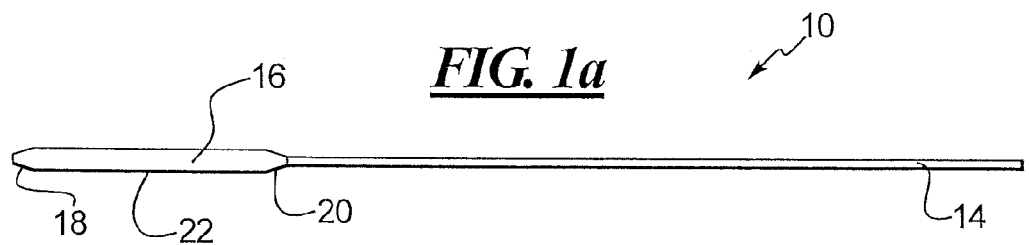
FIG. 1a illustrates a first exemplary embodiment of a control tip in accordance with the present invention.

Referring to the drawing figures, like reference numerals designate identical or corresponding elements throughout the several figures.

In the context of the present invention, "pledget" means a piece of sponge formed into a generally elongated shape having a size which allows delivery in a hydrated state through a delivery cannula or introducer to a site of a puncture in a blood vessel.

"Sponge" means a biocompatible material which is capable of being hydrated and is resiliently compressible in a hydrated state. Preferably, the sponge is non-immunogenic and may be absorbable or non-absorbable.

"Absorbable sponge" means sponge which, when implanted within a human or other mammalian body, is absorbed or resorbed by the body.

"Hydrate" means to partially or fully saturate with a fluid, such as saline, water, contrast agent, thrombin, therapeutic agents, or the like.

FIG. 1a illustrates a puncture control tip 10 in accordance with a first embodiment of the present invention. The puncture control tip 10 includes a tubular, hollow puncture control tip shaft 14, which functions as a flash tube, as described in greater detail below. The shaft 14 includes a lumen 34 (see FIG. 1c, for example) which extends longitudinally between proximal and distal ends. For reasons which will be readily appreciated by one of ordinary skill in the art, lumen 34 can optionally be coated or otherwise provided with an interior surface which inhibits blood coagulation. By way of example and not of limitation, the lumen 34 can be coated with material including heparin (e.g. heparinized), tPa, or other functionally similar materials or compounds which inhibit or prevent blood from clotting or otherwise coagulating in the lumen 34.

The puncture control tip 10 includes, at its distal end, a hollow puncture control head 16 mounted or otherwise secured to distal portions of the shaft 14. As illustrated in FIG. 1a, the head 16 includes a distal tapered portion 18, a proximal tapered portion 20, and a center portion 22 between the distal and proximal portions which preferably has a constant outer diameter. Both of the portions 18 and 20 can alternatively be a step, rounded shoulder, or the like. The interior of head 16 is open to the exterior of the head at the distal portion 18 (see, e.g., FIGS. 1c and 1d).

Figure 1B:
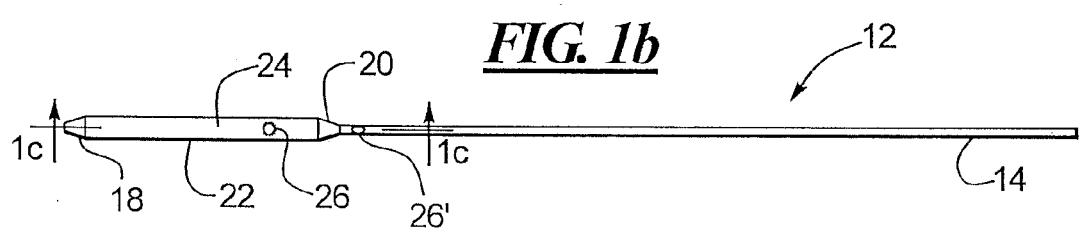
FIG. 1b illustrates a second exemplary embodiment of a control tip in accordance with the present invention.
Figure 1C:
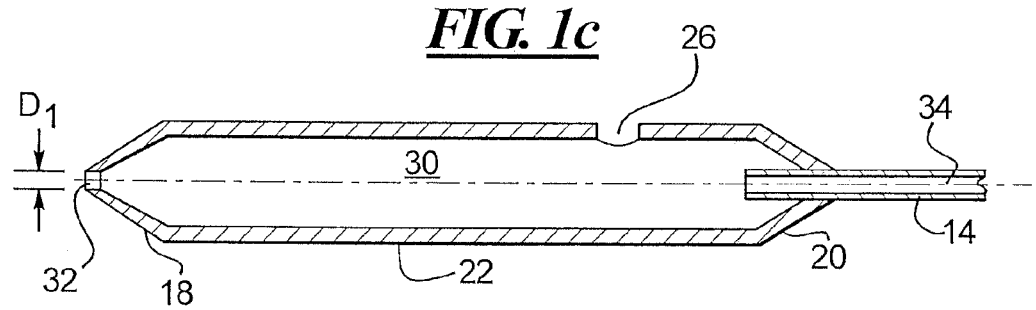
FIG. 1c illustrates an enlarged cross-sectional view of a third exemplary embodiment of a control tip in accordance with the present invention, taken at line 1—1.
Figure 1D:
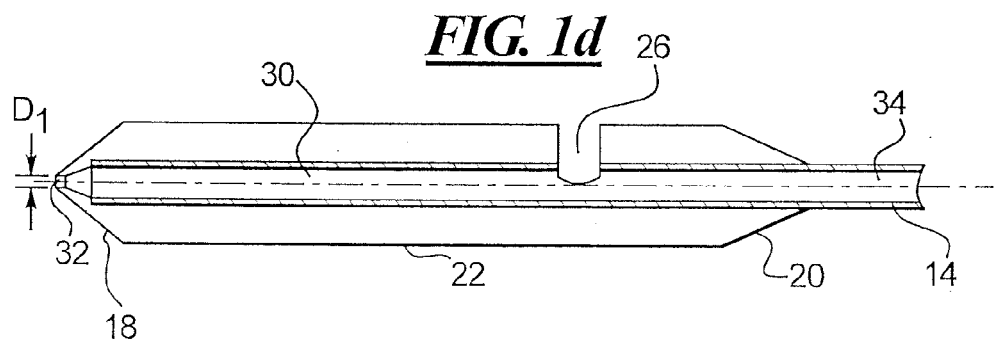
FIG. 1d illustrates an enlarged cross-sectional view of a third exemplary embodiment of a control tip in accordance with the present invention, taken at line 1—1.

FIG. 1b illustrates another embodiment of a puncture control tip 12 in accordance with the present invention. The control tip 12 is similar to control tip 10, but includes a puncture control tip head 24 which includes a hole 26 which communicates the exterior of the head with the interior thereof and functions as a flash hole or vent for the control tip. According to yet another embodiment, a hole 26' can be included in addition to, and preferably instead of, hole 26. Hole 26' is formed in the shaft 14 proximal of and proximate to the proximal portion 20, and communicates the interior lumen of the shaft with the exterior of the shaft. Turning to FIGS. 1c and 1d, further embodiments of heads 16 and 24 are illustrated as cross-sectional views taken at line 1—1 in FIG. 1b. Shaft 14 includes lumen 34 which fluidly communicates the interior 30 of heads 16, 24 with a proximal end of the shaft. The lumen 34 has an inner diameter selected to be larger than the external diameter of a guidewire, preferably an exchange wire 28, used therewith (see FIG. 2). Furthermore, a plurality of holes 26 (not illustrated) can be formed in the control head, circumferentially spaced and at the same longitudinal location as hole 26.

As illustrated in FIG. 1c, head 16, 24 can be relatively thin walled such that the internal dimensions of the interior cavity 30 is larger in center portion 22 than in the distal 18 and proximal 20 portions of the head. As also described briefly above, the distal portion 18 of head 16, 24 includes a distal port 32 having an internal opening diameter $D_1$ also selected to be larger, and preferably only slightly larger, than the external diameter of a wire 28 used with the control tip 10, 12. While the function of port 32 in conjunction with wire 28 will be described in greater detail below, one aspect of the present invention is that by selecting the external diameter of wire 28 and the inner diameter of port 32 to be only slightly different, blood flow into interior 30 of head 16, 24 is greatly restricted, thus allowing the hole 26 to be the sole entrance into the control tip for blood to flow up shaft 14 to indicate that the control tip head has been located in a blood vessel. As illustrated in FIG. 1d, the head 16, 24 can be formed with a thick wall, such that the interior chamber 30 is the same size as port 32.

Preferably, the control tip is formed of a flexible, biocompatible material, such as thermoplastic. By way of example and not of limitation, the material out of which the control tip is formed has a Shore hardness between about 90A–82D, preferably between about 98A–74D, more preferably about 64D.

Figure 2:
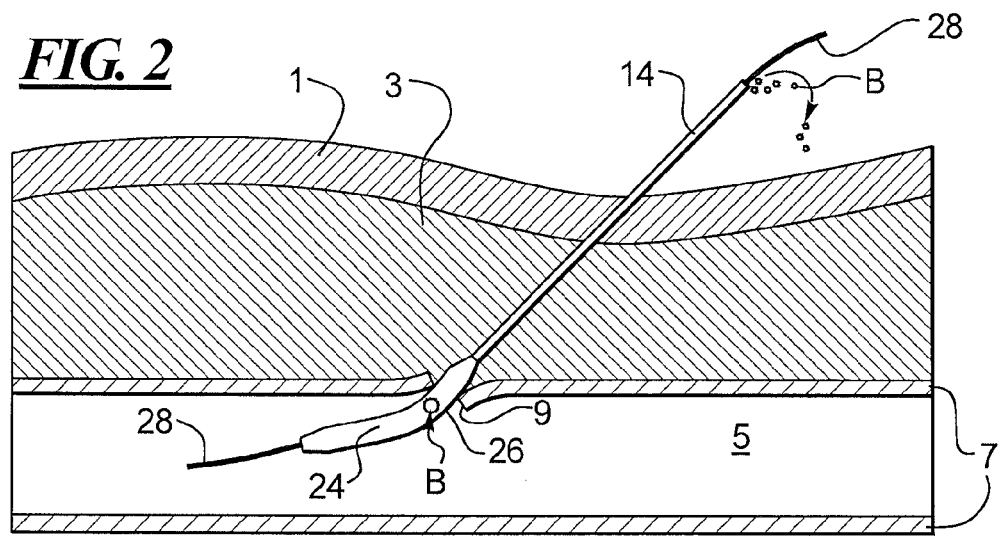
FIG. 2 schematically illustrates portions of a system in accordance with the present invention positioned in a blood vessel of a patient.

Turning now to FIG. 2, some functions of control tips in accordance with the present invention can be better appreciated. As discussed above, at the end of a endoluminal, transvascular procedure the practitioner will oftentimes want to seal the access point to the patient's vasculature. As is commonplace when using a Seldinger technique for vascular access, a guidewire, exchange wire, or guide catheter remains in the patient's blood vessel 5 at the end of the procedure. The indwelling device extends through the epidermis layer 1, through the subcutaneous layers 3, and enters the vessel wall 7 at a puncture site 9.

A control tip 12 (as illustrated in FIG. 2, although control tips 10 can also be used) is advanced either through an indwelling guide catheter, or over an indwelling wire 28, until blood B enters hole 26. The blood B flows into interior 30 of the control head 24, through lumen 34 and around the wire 28, and exits the shaft 14 at its proximal end. This flash of blood at the proximal end of shaft 14 gives the practitioner a visual indication that the control tip is seated in the puncture site 9, while the placement of the hole 26 distal of the proximal portion 20 assists in maintaining the puncture site closed during the procedure. As discussed above, because port 32 has an inner diameter selected to be only slightly larger than the outer diameter of wire 28, little or no blood enters into the interior 30 of the head 24 between the wire and port. Also, the distance between the hole 26 and the proximal end of the vent tube 14, and the internal diameter of the vent tube, are selected together to prevent a capillary effect by the inner wall of the vent tube from stopping blood flow while still permitting good flexibility of the vent tube. Additionally, the vent tube 14 can optionally be formed to have a flexibility which changes along its length, e.g., is more flexible at distal portions than at proximal portions. While a gradual distal increase in flexibility is preferred, the change can be more abrupt, such as by forming the vent tube 14 of two distinct tubes of different flexibilities, although this later embodiment is less preferred.

Figure 3A:
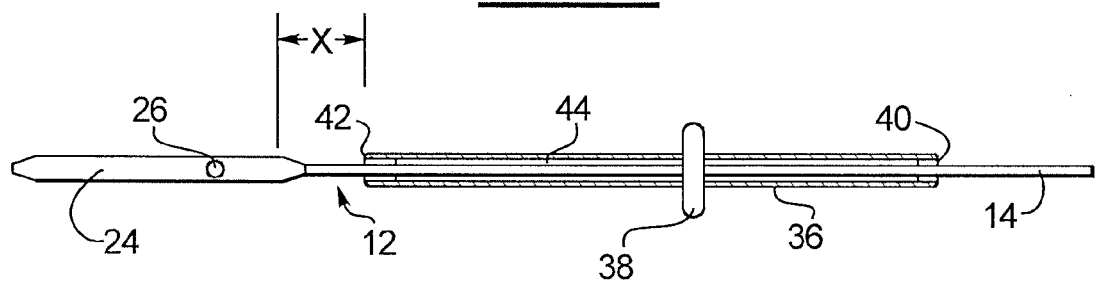
FIG. 3a illustrates a side elevational view of portions of a first exemplary system in accordance with the present invention.

FIG. 3a illustrates an embodiment of a depth marker 36 mounted over a control tip 12 in accordance with the present invention. Marker 36 is a hollow, tubular member preferably shorter than the control tip 12. Marker 36 optionally further includes a collar 38 slidable along the outer surface of the marker. The collar 38 is preferably elastic such that it will engage the exterior of the marker 36 to hold its position on the marker, yet be movable along the marker upon the application of a small force to slide the collar along the marker. Thus, collar 38 can be used as a depth indicator, as described in greater detail below.

The marker 36 includes a proximal end 40, a distal end 42, and an interior lumen 44 extending longitudinally between the proximal and distal ends. The proximal and distal ends of the marker 36 preferably include a seal with the shaft 14 of the control tip 12. The seal between the shaft 14 and the marker 36 can be formed in any suitable way that provides a fluid seal between the marker and the shaft. By way of example and not of limitation, the proximal and distal seals can be formed by forming the marker with a reduced inner diameter at (at least) the proximal and distal ends of the marker, or by including dynamic sealing members, such as O-rings or septa. Preferably, at least the distalmost portions of distal end 42 is slightly rounded to prevent trauma to the vascular tissues with which it comes into contact.

Marker 36 is preferably attached to control tip 12, or less preferably, positioned on the control tip 12 so that it is difficult to slide them longitudinally relative to each other. The distal end 42 is spaced from the elongated central portion 22 of the control head by a distance X, described in greater detail below. Optionally, the control tip and the marker can be interconnected using a releasable proximal connection, e.g. a Touhy-Borst connector (for which the marker would include cross-drilled holes or the like for blood flash), ultrasonic welding, gluing, etc.

Figure 3B:
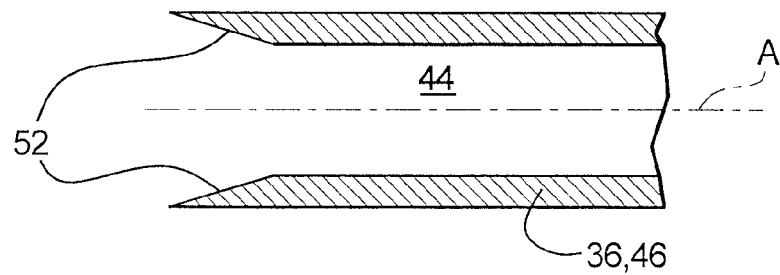
FIG. 3b illustrates an enlarged cross-sectional view of a portion of the exemplary embodiment of a pusher illustrated in FIG. 3a in accordance with the present invention.

FIG. 3*b* illustrates an enlarged cross-sectional view of a distal end of a marker 36 or 46 in accordance with the present invention. The marker includes an interior lumen 44 which terminates at the distal end 52 of the marker with a countersunk tapered distal port. For reasons which will be explained in greater detail below with reference to FIGS. 5 and 6, the taper of the distal port relative to longitudinal axis A is selected to be very similar to that of the proximal tapered portion 20 of head 16, 24. This aspect of the present invention permits the wall of the marker 36, 46 which forms the port, together with the proximal tapered portion 20, to function as a valve in a manner similar to a needle valve.

FIG. 4 illustrates a control tip 12 used together with a depth marker 36 to control a puncture site 9. When the control tip 12 has been located in the puncture site 9, as shown by the blood flash B out the proximal end of flash tube 14, with the marker 36 on the shaft 14 the practitioner feels the additional resistance offered by the vessel wall 7 to further advancement of the marker upon distal advancement of the control tip/marker assembly. As the distal end 42 of the marker 36 forms a seal with the shaft 14, the distal end 42 can then be used to control the flow of blood out of the puncture site 9, and the control head 24 is pushed slightly distally into the blood vessel 5. Collar 38 can be positioned against the epidermis 1 when the distal end 42 is at the puncture site 9, which permits the collar 38 to mark the distance between the distal end of the marker 36 and the outer surface of the epidermis, thus functioning as a depth indicator of the puncture site.

Turning now to FIGS. 5 and 6, yet another embodiment in accordance with the present invention is illustrated. FIG. 5 illustrates a control tip 10 with head 16 and a marker 46 mounted thereover. Marker 46 is similar to marker 36, described above, but does not include seals at its proximal 50 and distal 52 ends. A lumen 48 extends longitudinally through the marker 46 between the proximal and distal ends and forms an annular space or lumen 54 between the flash tube or shaft 14 and the marker 46. According to a preferred embodiment of the present invention, distal end 52 is tapered as illustrated in FIG. 3*b*. Marker 46 is affixed to control tip 10 in a fashion similar to marker 36 and control tip 12, described above.

FIG. 6 illustrates a marker 46 used in accordance with one aspect of the present invention with a control tip 10. While control tip 12 can also be used, the function of flash hole or holes 26 is assumed by the combination of proximal tapered portion 20 of head 16 and the distal end 52 of marker 46, optionally further including a tapered countersunk port therein. In a manner similar to that described above with reference to FIG. 4, the marker 46 can be used to control puncture site 9. By moving the assembly of the control tip 10 and the marker 46 longitudinally, the distal end 52 of the marker 46 and the proximal tapered portion 20 of the head 16 can be used to throttle the flow of blood into the annular lumen 54 in a manner similar to a needle valve. That is, by drawing the head 16 closer to the puncture site 9, the flow cross-sectional area is made smaller, thereby reducing the flow of blood into the lumen 54, and pushing the assembly distally increases the flow area, increasing the flow of blood. As the proximal end 50 is not sealed with shaft 14, blood flash B can be observed out of the proximal end of the marker 46, indicating that the marker is in fluid communication with the blood vessel 5. Furthermore, as wire 28 and port 32, as described above, permit little or no blood to flow into lumen 34 of the shaft 14, the blood flash B at proximal end 50 can be a reliable indicator that the blood vessel has been accessed.

In the embodiments of FIGS. 3*a*–6, it is preferable that the distal end of the depth marker has significant radial or lateral clearance from the control tip shaft, so that the two elements will move laterally relative to each other near the marker's distal end, which promotes tactile feedback to the practitioner when the control tip enters the blood vessel.

Figure 7:
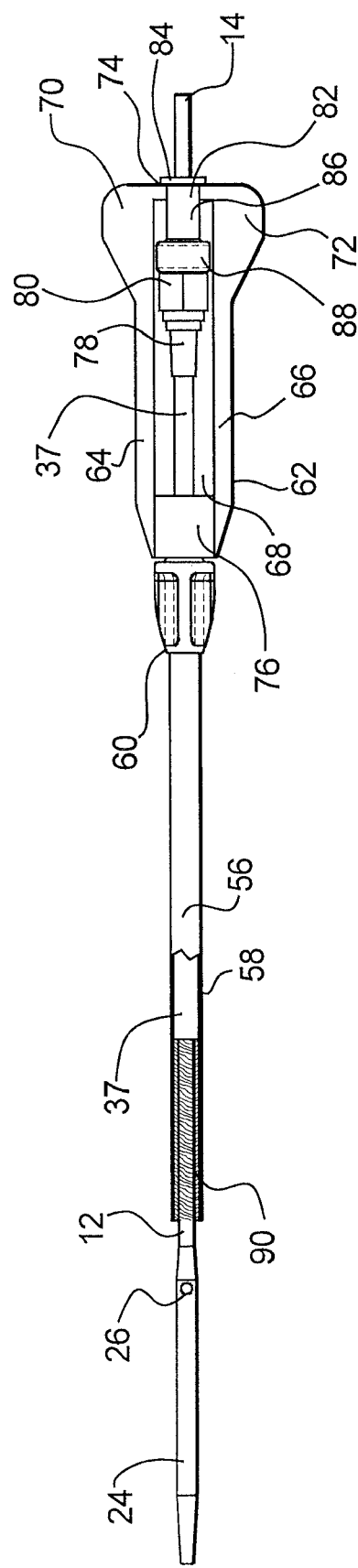
FIG. 7 illustrates a side elevational view of a system in accordance with the present invention.

FIG. 7 illustrates a side elevational view of a system in accordance with the present invention. The system generally includes a control tip 10 or 12, a pledget pusher 37, a delivery cannula 56, a pledget 90, and a proximal handle 62. As illustrated in FIG. 7, pledget 90 is positioned in a lumen 58 in delivery cannula 56 and around shaft 14 of control tip 12. Pusher 37 is also positioned in lumen 58, and has a length such that, when the pusher is in a retracted, proximal position illustrated in FIG. 7, the distal end 42, 52 of the pusher is proximal of the distal end of the delivery cannula 56. A pledget 90 is positioned in the distal portion of the lumen 58 distal of the distal end of the pusher 37 so that the pusher can push the pledget distally out of the delivery cannula. Pledget pusher 37 is structurally very similar to either pusher 36 or pusher 46, but is not attached to the control tip 10, 12 over which it longitudinally slides.

The pledget 90 according to one preferred embodiment of the invention is formed from a sheet of absorbable sponge material which has been cut into a rectangular shape and rolled to form a compact, substantially cylindrical, elongated pledget. One type of absorbable sponge material which is acceptable for use in the present invention is Gelfoam™, manufactured by the Pharmacia & Upjohn Company. Gelfoam™ is a porous, pliable, cross-linked gelatin material and is available commercially in sheet form as pre-compressed or non-compressed sponge. The material may be provided preformed as a pledget 90 or may be cut with a punch, or a stencil, or template and knife and rolled to form a pledget. Once hydrated, the pledget 90 can be easily compressed to fit into a lumen having a smaller cross sectional area than the original cross sectional area of the pledget. Additionally, the kneading of the hydrated pledget 90 during delivery encourages air trapped within the Gelfoam™ to be expelled and replaced with fluid, allowing rapid expansion upon delivery. When a pledget 90 of a pre-compressed Gelfoam™ is hydrated and kneaded (expelling air) during delivery, the pledget will have the absorption capacity to rapidly expand to many times (e.g., 3 or more times) its original dry volume upon delivery. When a pledget 90 of the non-compressed Gelfoam™ is hydrated and kneaded (expelling air) during delivery, the pledget will have the absorption capacity to rapidly expand to its original dry volume upon delivery. These properties make the Gelfoam™ sponge material particularly useful for facilitating hemostasis of puncture sites by injection.

The delivery cannula 56 includes a proximal hub 60. Hub 60 includes mating structures to mate with corresponding mating structures formed in a distal hub 76 of handle 62. By way of example and not of limitations, the mating structures of hub 60 and hub 76 can be luer fittings, screw threads, releasable bayonet fittings, and any other fitting which can releasably connect together hubs 60, 76 so that the delivery cannula 56 and the handle 62 can be moved together when the structures are mated, and the delivery cannula and handle can be separated and moved independently when the structures are released.

Pusher 37 includes a proximal hub 78 which both limits the proximal and distal movement of the pusher, and provides an enlarged section at which a practitioner can grasp the pusher if necessary. Hub 78 optionally further includes a proximal outwardly flared stop 80 which limits longitudinal motion of the pusher 37 relative to the handle 62 and other structures of the system, described in detail below. More particularly, stop 80 limits distal motion of the pusher 37, because it has an outer dimension (e.g., diameter) larger than portions of hub 76 of handle 62, and limits proximal motion because the stop is longitudinally aligned with portions of a motion limiting device 82 (described below) positioned proximal of the stop.

Handle 62 generally provides a place for a practitioner to grasp and manipulate the control tip 12, pusher 37, and delivery cannula 56 together, while also permitting the practitioner to separately move these individual components. Therefore, while a particular embodiment of a handle in accordance with the present invention is illustrated in FIG. 7, the present invention relates more generally to structures which performs these functions.

Handle 62, as illustrated in FIG. 7, includes a first side 64, a second side 66, and an open interior space 68. By providing handle 62 with an open construction, such as that illustrated in FIG. 7, a practitioner is able to access the proximal portions of pusher 36, 46 and control tip 12 in order to manipulate these elements. Each of the sides 64, 66 includes a wing 70, 72, respectively, which is optionally further provided to provide a bearing surface for a practitioner to pull the handle and any attached elements proximally.

The proximal end of the handle 62 includes an opening, slot, or the like 74 which receives a proximal motion limiting device 82 for the control tip 12. In the embodiment illustrated in FIG. 7, device 82 includes a proximal flange 84 which extends radially beyond the extent of opening 74, and therefore limits distal motion of the device 82 as it slides in the opening 74. The device 82 also includes a central cylindrical portion 86 which longitudinally slides in opening 74. A distal bumper 88 of device 82 is also radially larger than opening 74, and limits proximal motion of the device 82 relative to the handle 62. The flash tube or shaft 14 is secured to and preferably extends proximally through device 82, as illustrated in FIG. 7. Thus, the entire control tip 12 is permitted to move longitudinally over a limited range delimited by the proximal flange 84 and the distal bumper 88. Because the control tip 12 is therefore permitted to move longitudinally over only a limited-range defined by device 82, and handle 62 is attached to delivery cannula 56 via hubs 60 and 76, the control tip is capable of moving longitudinally over only a limited range relative to the delivery cannula. The magnitude of range X (see FIGS. 3a, 5, and 8A) is between about 0.025 inches (0.06 cm) and about 0.25 inches (0.6 cm), preferably between about 0.1 inches (0.25 cm) and about 0.2 inches (0.51 cm), and more preferably about 0.15 inches (0.38 cm).

As will be readily appreciated by one of ordinary skill in the art, device 82 can take forms different from those illustrated in FIG. 7, while still performing the functions describe above. By way of example and not of limitation, device 82 and handle 62 can include other types of complementary surfaces, including mating threads, tabs and slots, and the like, within the scope of the present invention. Furthermore, opening 74 can be formed open on one lateral side, so that device 82 can be snapped into the handle 62 in a direction into or out of the plane of view of FIG. 7, thereby permitting assembly and disassembly of the handle with the other elements of the system. To facilitate this assembly and disassembly, it is advantageous to form at least the proximal portions of handle 62 of a resilient material which will deform to permit the device 82 to be snapped into the handle.

Figure 8A:
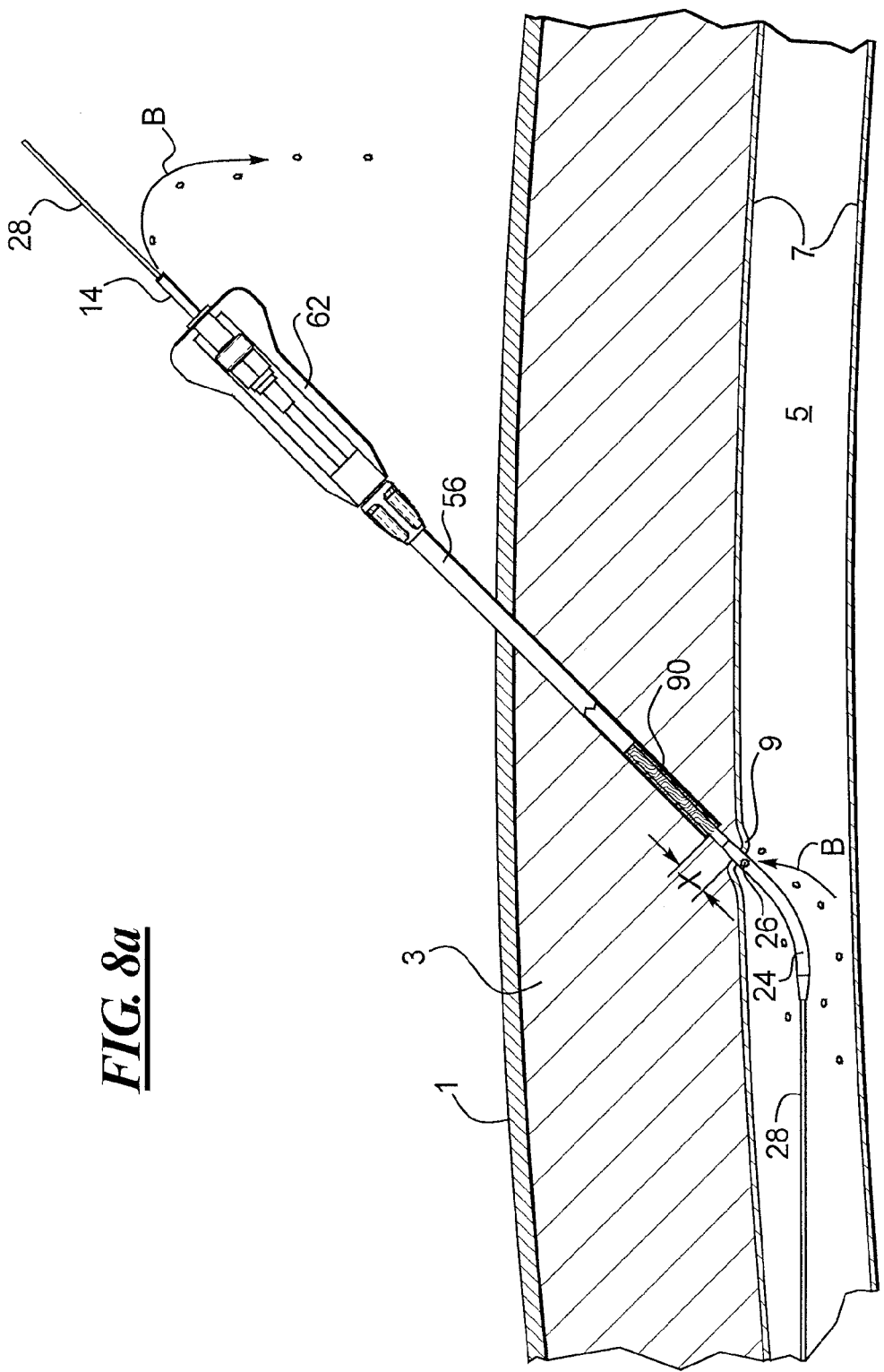

FIGS. 8a–8f illustrate a system as illustrated in FIG. 7 used in accordance with an exemplary embodiment of the present invention. After an endoluminal procedure which has been performed using, in part, a Seldinger technique for access to the patient's vasculature, a wire 28 is advanced into the patient's blood vessel 5 through a puncture site 9 in the vessel wall 7. A control tip 12, pusher 37, delivery cannula 56, handle 62, and pledget 90 are advanced together over the wire 28, as illustrated in FIG. 8a. According to a less preferred embodiment, the control tip is first advanced over the wire and into the blood vessel, and thereafter the delivery cannula, handle, pusher, and pledget are advanced over the control tip. As the practitioner advances the system along the wire 28, the control head 24 passes through the puncture site 9. Because the vessel wall presents more resistance to the control head than the subcutaneous tissues 3, the practitioner can feel when the control head has reached the outer portions of the puncture site 9. The practitioner then advances the control head further into the patient and into the blood vessel 5.

When the hole 26 enters the blood vessel 5, blood B flashes out the proximal end of flash tube 14, as described above, indicating to the practitioner that entry to the blood vessel has been made. Because blood may have previously been present in lumen 34 of shaft 14, and therefore potentially has already clotted or coagulated, blocking the lumen 34, it is preferable that lumen 34 be coated with a blood anticoagulant, as described above. Another tactile indication to the practitioner that entry to the blood vessel 5 has been made is provided by the distance or gap X between the proximal end of the control head 24 and the distal end of the delivery cannula 56. Because the overall flexibility of the system between the proximal end of the control head 24 and the distal end of the delivery cannula 56 is less than both the longitudinally adjacent sections of the system, the practitioner can feel that the system is more easily moved laterally when the control head 24 is in the position illustrated in FIG. 8a. Conversely, when the practitioner does not feel this reduced resistance to lateral movement of the system, the practitioner has an indication that the blood vessel 5 has not been properly accessed.

FIG. 8b illustrates a stage in the exemplary method later than that illustrated in FIG. 8a. After the practitioner has accessed the blood vessel 5 as described above, the entire system is advanced down the wire 28, as suggested by the arrow in the figure. Advancement of the system is halted when the distal end of the delivery cannula 56 engages the outer portions of the puncture site 9. As described above, as the vessel wall 7 provides more resistance to advancement of the system than does the adjacent subcutaneous tissues, the practitioner can feel when the delivery catheter has engaged the vessel wall. Verification that the delivery catheter is properly engaged against the vessel wall 7, and not merely hung up on a somewhat more resilient anatomical structure within the subcutaneous tissues, is provided by blood flash out the proximal end of the flash tube 14. At this point, the puncture site 9 is controlled by the delivery cannula 56.

FIG. 8c illustrates a stage in the exemplary method later than that illustrated in FIG. 8b. After the delivery cannula has engaged the outer surface of the puncture site 9, the device 82

(described above) is pulled proximally relative to the handle 62 while the remaining elements of the system are held stationary. The control tip 12, including the control head 24, is retracted proximally and engages the inner surface of the vessel wall at the puncture site 9. Thus, both the interior and exterior surfaces of the vessel wall 7 are engaged by portions of the system, which controls blood flow out of the puncture site. As discussed above, access to device 82 is facilitated by the open structure of handle 62, permitting a practitioner to more easily pull the device 82 proximally relative to the handle 62. Additionally, as the control head 24 is positioned distally of the pledget 90 and controls access to the blood vessel through the puncture site 9, the pledget is inhibited, and preferably prevented, from entering the blood vessel. Thus, the present invention is also advantageous because it can be used to prevent introduction of all or portions of a pledget into the bloodstream of a patient, which could otherwise initiate a clotting sequence in the blood vessel, with predictably hazardous consequences to the patient.

Figure 8D:
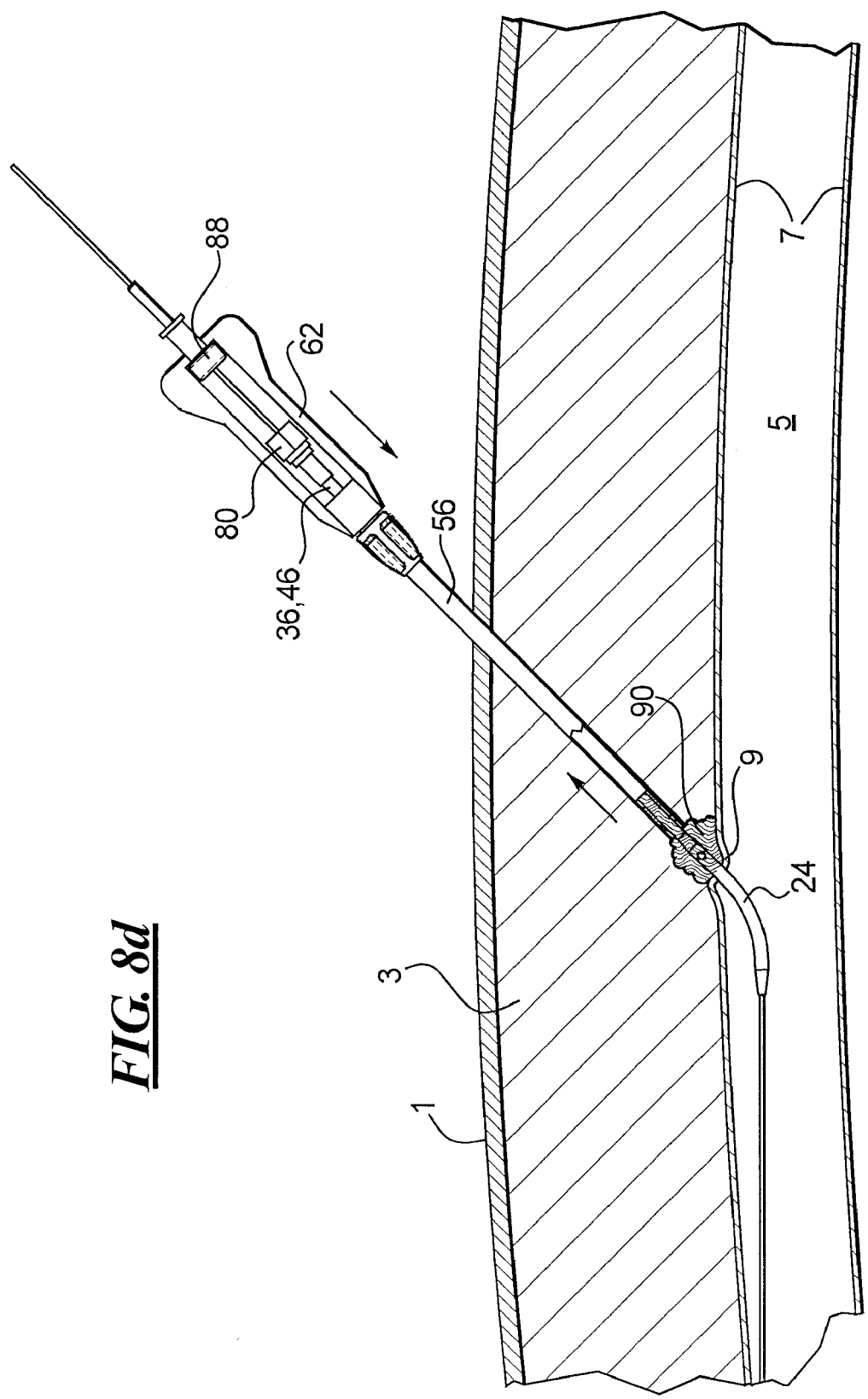

FIG. 8d illustrates a stage in the exemplary method later than that illustrated in FIG. 8c. The handle 62, delivery cannula 56, and control tip 12 have been retracted proximally, while holding stationary the pusher 37, such as by pulling proximally on the distal portions of bumper 88 while engaging the proximal portions of stop 80 to prevent its longitudinal motion. Proximal retraction of the delivery cannula 56 relative to the pusher 37 causes distal portions of the pledget 90 to be exposed, while at the same time the pusher does not move and is left positioned at the exterior surface of the blood vessel 5 at the puncture site 9. At the same time, proximal portions of the control head 24 are drawn through the distal portions of the pledget 90. It is preferable that the handle 62, delivery cannula 56, and control tip 12 are moved only part of the distance necessary to completely expose the pledget 90 and for stop 80 to engage portions of hub 76, as illustrated in FIG. 8d, so that the pledget can be expressed and compressed, as described below with reference to FIG. 8e.

Figure 8E:
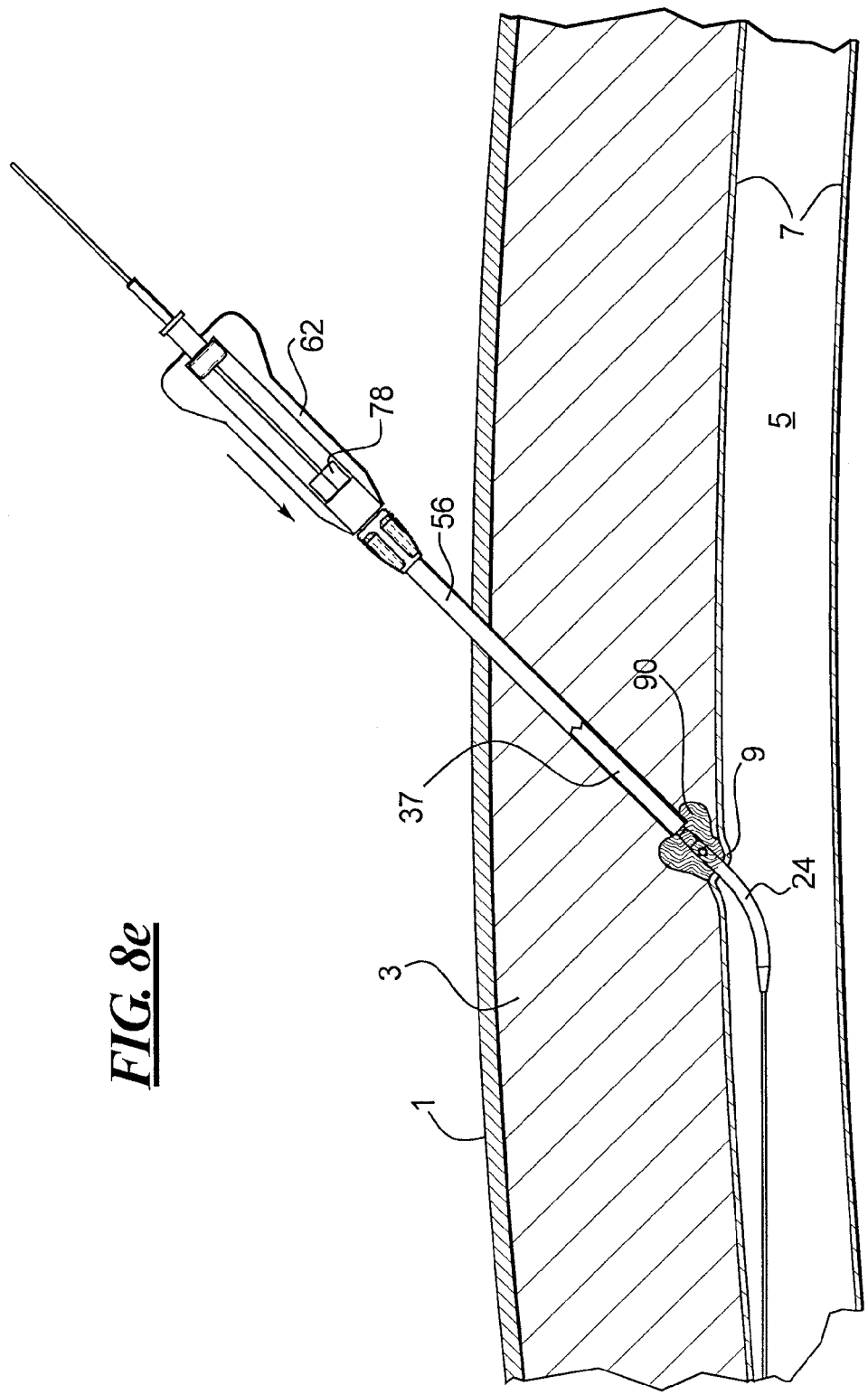

FIG. 8e illustrates a stage in the exemplary method later than that illustrated in FIG. 8d. While holding handle 62 stationary relative to the patient, the pusher 37 is advanced distally down the control tip 12, which expels or pushes the remainder of the pledget 90 out of the lumen 58 and simultaneously compresses the pledget against the external surface of the blood vessel wall 7 at the puncture site 9. During this expulsion process, the control head 24 is positioned in the puncture site 9, and therefore at least inhibits, and preferably prevents, the pledget 90 from being pushed into the blood vessel 5. In this manner, the puncture site 9 is controlled throughout the steps of positioning the pledget 90 adjacent to the exterior of the puncture site and both inhibits bleeding and inhibits the introduction of material, including the pledget 90 as well as tissue fragments, into the blood vessel.

Figure 8F:
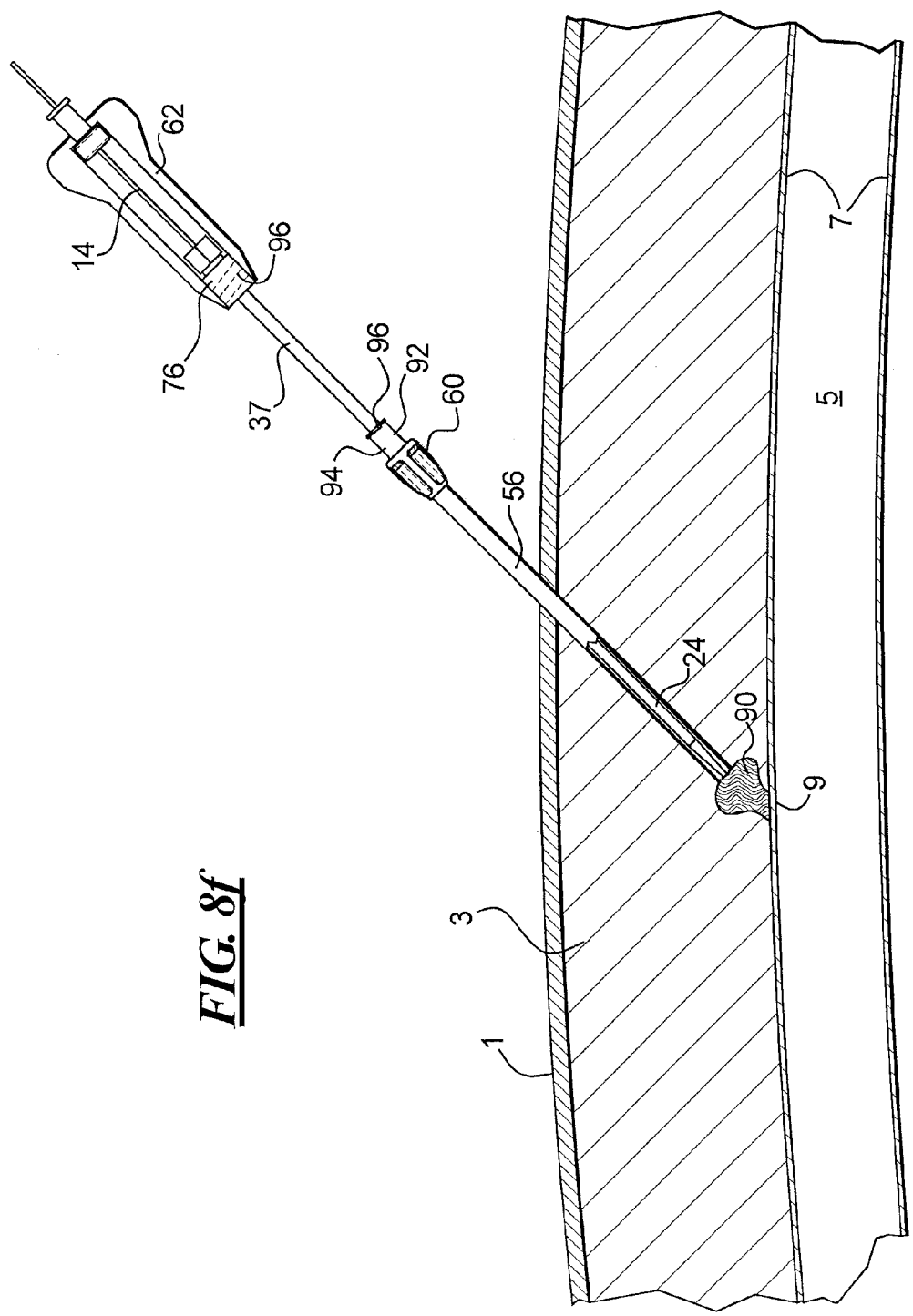

FIG. 8f illustrates a stage in the exemplary method later than that illustrated in FIG. 8e. The handle 62 is released from its connection with the delivery cannula 56 by releasing the connection between hub 76 and hub 60. The handle is then retracted proximally, carrying with it the control tip 12 and the pusher 37. The delivery cannula 56 is preferably held stationary in the patient during this retraction, so that the delivery catheter can hold the pledget 90 in place. As the control head 24 is pulled out of the puncture site 9, the site is compressed by the pledget 90, which inhibits bleeding and promotes closure of the puncture site. As the control tip 12 is further retracted, the control head 24 is drawn through the pledget, while the delivery cannula inhibits the pledget from following the control tip back up into the delivery cannula. The handle, pusher, and control tip are then completely removed. Then, the delivery cannula is removed, preferably slowly and with the application of localized compression to the epidermis above the puncture site, leaving the pledget 90 in place to promote healing of the puncture site 9 and inhibit blood flow from the blood vessel.

Also illustrated in FIG. 8f is an exemplary embodiment of the mating structures of hubs 60 and 76 which releasably hold together the handle 62 and the delivery cannula 56. As illustrated in FIG. 8f, hub 60 includes a mating structure 92, e.g., a tubular extension 94 including a tab 96 extending radially therefrom. Hub 76 includes an internally threaded collar 96 which receives the extension 94 therein and secures the two elements together.

Figure 9:
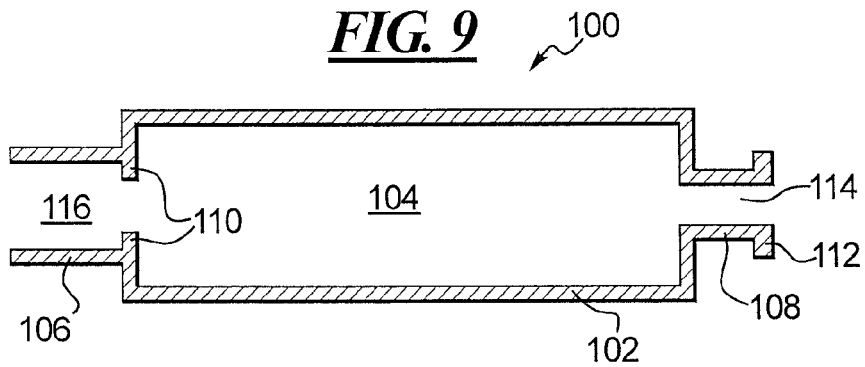
FIG. 9 illustrates a cross-sectional view of a pledget hydration chamber in accordance with an exemplary embodiment of the present invention.

FIG. 9 illustrates an exemplary embodiment of a pledget loading device 100 useful for preparing a pledget 90 and loading the pledget into a delivery cannula. As illustrated in FIG. 9, the pledget loading device 100 includes a body 102 having an interior chamber 104. A tubular receiving element 106 extends distally from the distal end of the body, and includes a lumen 116 therein communicating the interior chamber 104 with the exterior of the body. A fluid coupling 108 extends proximally from the end of the body opposite the element 106, and includes a flange, tab, or the like 112 and an internal lumen 114 which communicates the interior chamber 104 with the exterior of the body. The flange 112 is structured to releasably mate with a corresponding structure on a high pressure fluid delivery device, e.g., a syringe with a luer fitting. The body 102 also includes a stop 110 positioned in the lumen 116 which prevents a delivery cannula of a size greater than the internal dimension of the stop from entering into the chamber 104.

Figure 10:
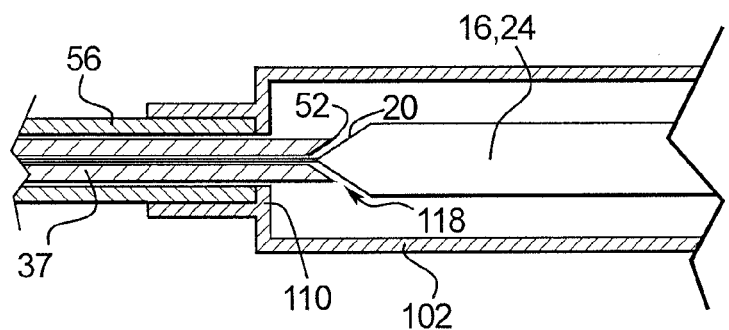
FIG. 10 illustrates the chamber of FIG. 9 with portions of a device of FIG. 7.

FIG. 10 illustrates the pledget loading device 100 with a delivery cannula 56, pusher 37, and a control tip 12 inserted into the tubular receiving element 106. As described above, stop 110 is sized so that the delivery cannula 56 is prevented from entering into the chamber 104, and preferably forms a fluid seal with the stop 110, the inner surface of the element 106, or both. The pusher 37 and the control tip 12 extend into the chamber 104. The combination of the tapered countersunk distal end 52 of the pusher and the tapered proximal portion 20 of the control head 16, 24 form a fluid control member 118 which operates in a manner similar to a needle valve. The operation of fluid control member 118 will be described in greater detail below.

Figure 11:
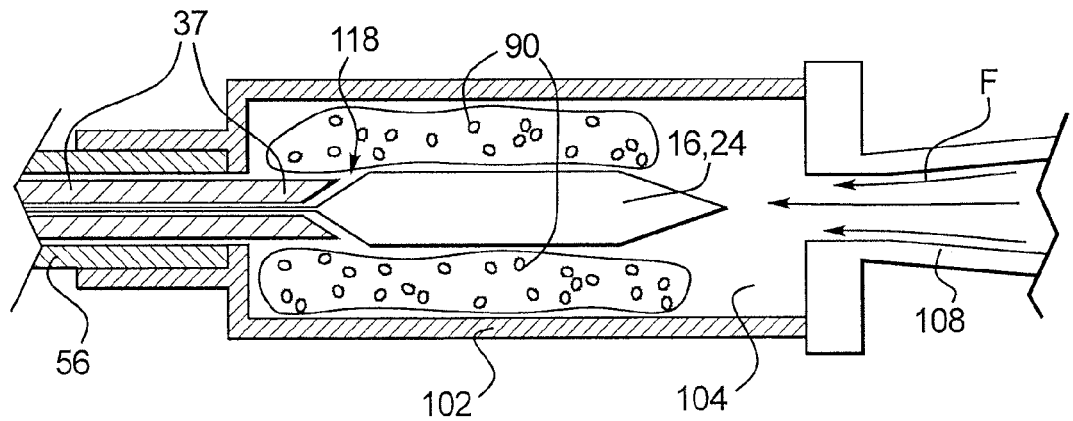
FIGS. 11–13 illustrate exemplary steps of hydrating, preparing, and positioning a pledget into a delivery device in accordance with an exemplary embodiment of the present invention.
Figure 12:
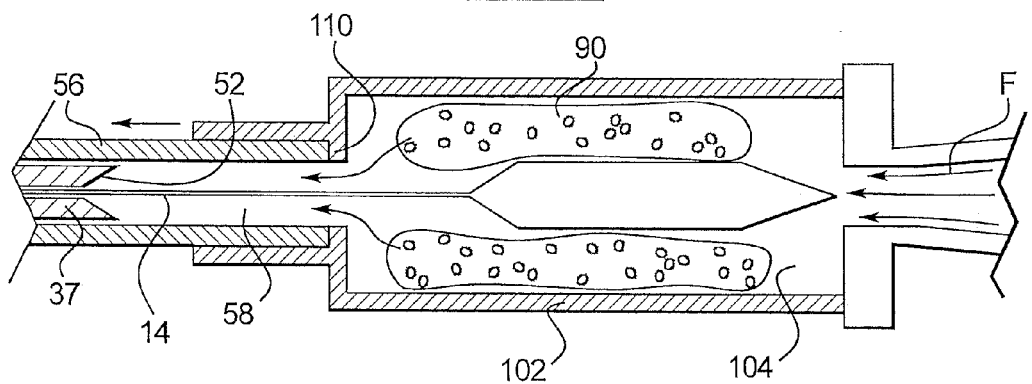
Figure 13:
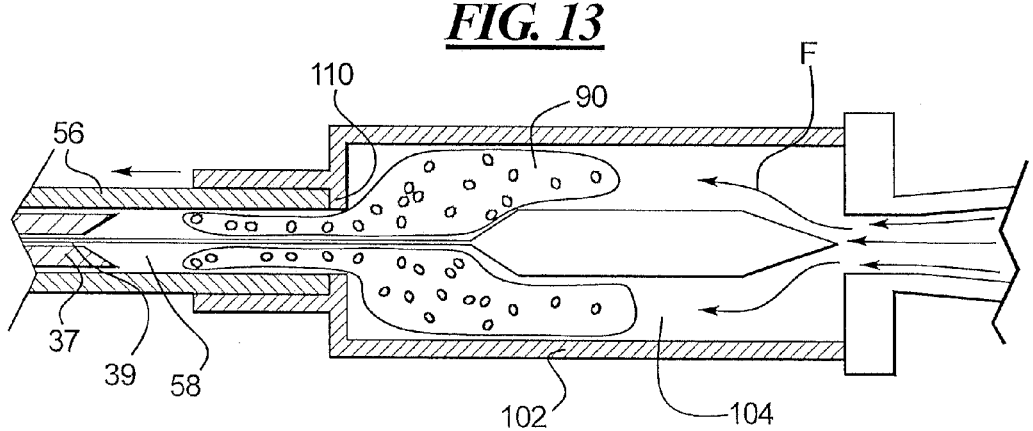

In FIG. 11, a cylindrical pledget 90 has been inserted into the chamber 104. The pledget can be placed in the chamber 104 before or after the control head 16, 24 is positioned in the chamber. A source of hydration fluid, such a syringe (not illustrated), is coupled to fluid coupling 108, and hydration fluid F is injected into the chamber 104. Air in the chamber 104 is allowed to escape through fluid control member 118, while the pledget 90 is retained in the chamber and hydrated. As illustrated in FIG. 12, to assist in hydrating the pledget 90, the pusher 37, is retracted into the lumen 58 of the delivery cannula 56, in effect opening the fluid control member 118. Air and hydration fluid are then allowed to flow past the stop 110, through the lumen 58, through the lumen 39 of pusher 37, and out of the system. As illustrated in FIG. 13, the further introduction of high pressure fluid into chamber 104 forces the hydrated pledget 90 past the stop 110 and into the portion of lumen 58 not occupied by the pusher 37, while hydration fluid continues to flow out the lumen 39. In this manner, the hydrated pledget 90 is loaded into the end of the delivery cannula 56.

Figure 14:
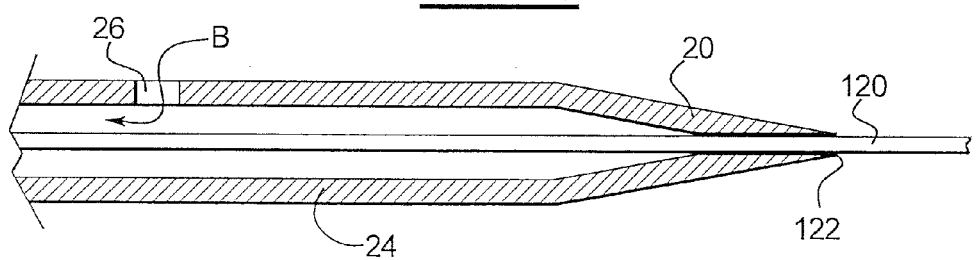
FIG. 14 illustrates a cross-sectional view of yet another embodiment of a control tip device in accordance with the present invention.

FIG. 14 illustrates yet another embodiment of a control head in accordance with the present invention. As illustrated in FIG. 14, a constant outer diameter guidewire 120 is slidingly received in the tapered distal portion 20 of a control tip 24. At the distalmost end of the distal portion 20, the guidewire 120 and the tapered portion 20 are nearly the same size, so that there is little or no blood flow into the interior 30 of the control head 24 past the guidewire. Such an arrangement helps assure that any blood flow into the flash tube 14 (see FIGS. 1a–1d) enters the control head 24 through the hole 26.

Figure 15:
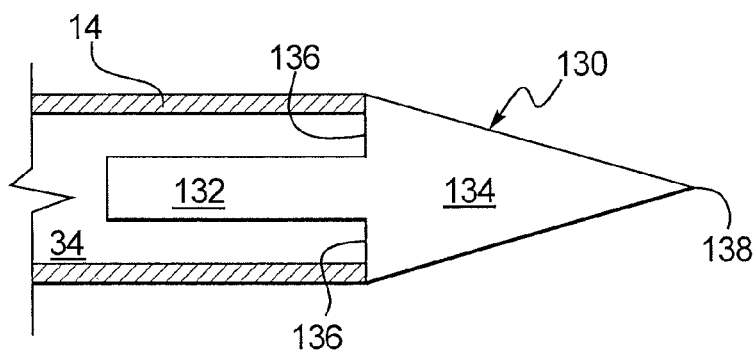
FIG. 15 illustrates a cross-sectional view of yet another embodiment of portions of a control tip device in accordance with the present invention.

FIG. 15 illustrates yet another embodiment in accordance with the present invention. The proximal end of shaft 14 is fitted with a removable insertion tip 130 so that the proximal end of the shaft, with the tip 130 mounted in the shaft as illustrated in FIG. 15, can be backloaded through a pledget (not illustrated) held within a distal end of a delivery cannula (not illustrated). The insertion tip, in the embodiment illustrated in FIG. 15, includes a shank 132 and a head 134 attached to the shank. The shank has an outer dimension (e.g., diameter) sized to be received in the lumen 34 of the shaft 14, and can be large enough to form an interference or press fit with the shaft. The shank 132 and the head 134 meet at a shoulder 136 which abuts the proximalmost end of the shaft 14. The head preferably includes a pointed or otherwise tapered tip 138 which assists in moving portions of the pledget radially outward when the shaft and insertion tip 134 are pushed longitudinally through the pledget.

Figure 16:
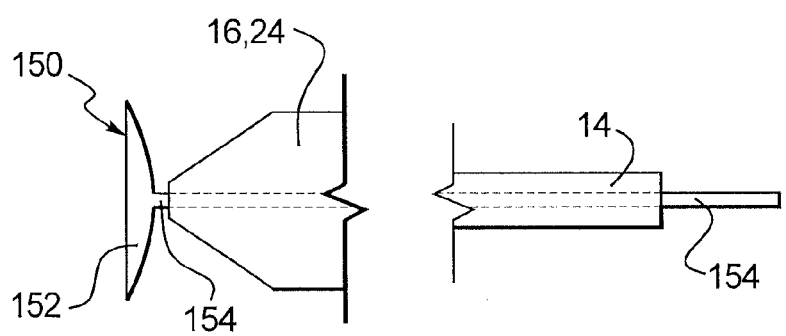
FIG. 16 illustrates a cross-sectional view of yet another embodiment of portions of a control tip device in accordance with the present invention.

FIG. 16 illustrates yet another embodiment in accordance with the present invention. A stylet 150 is inserted through a control tip 10 or 12 and assists in inserting the control tip through a pledget (not illustrated) positioned inside a delivery cannula (not illustrated). The stylet 150 includes a head 152 and a shaft 154 connected to and extending from the head. The shaft 154 is sized to slide through the control tip and shaft 14. The head 152 is enlarged to facilitate pushing on the head to push the proximal end of the shaft 14 through a pledget; the shaft 154 extends from the proximal end of the shaft to assist is radially parting the material of the pledget.

Figure 17:
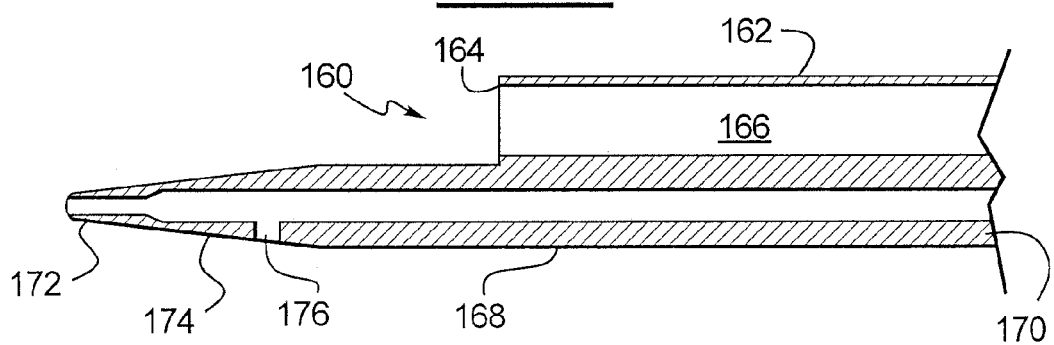
FIG. 17 illustrates a cross-sectional view of yet another embodiment in accordance with the present invention.

FIG. 17 illustrates yet another embodiment in accordance with the present invention, in which a delivery cannula 160 includes a control tip 168 integral with the delivery cannula. The delivery cannula 160 has a tubular wall 162 which extends longitudinally between a proximal end 162 and a distal end 164, which distal end is preferably rounded to ease its insertion through subcutaneous tissues and limit trauma to the vascular wall when it is pressed against it. A lumen 166 extends through the delivery cannula 160 between the proximal end 162 and the distal end 164, and is sized in a manner similar to the other embodiments described herein to receive a pledget, pledget pusher, and/or wire.

Figure 18:
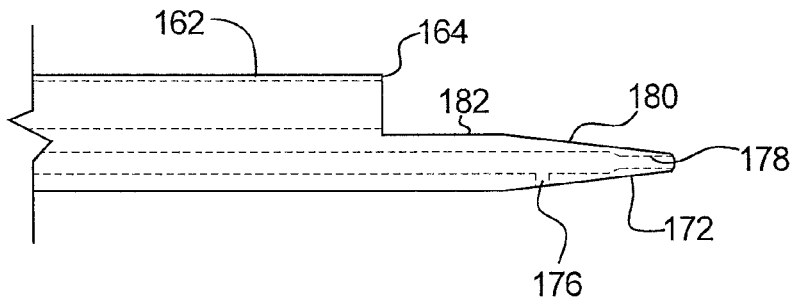
FIG. 18 illustrates a cross-sectional view of yet another embodiment in accordance with the present invention.

Formed integrally with the delivery cannula 162, the control tip 168 extends longitudinally between a proximal end 170 and a distal end 172 radially offset from the center longitudinal axis of the lumen 166. The control tip 168 includes a longitudinally extending lumen 174 and a vent port or hole 176 similar to hole or holes 26. As in other embodiments described herein, the distal end 172 is preferably tapered, and preferably has an inner diameter which tapers distally, as at 178, to form a dynamic seal with a wire (not illustrated) over which the control tip 168 is inserted. As illustrated in FIG. 18, the external taper 180 of the distal end of the control tip 168 can extend proximally toward the delivery cannula 160, and the vent hole 176 is preferably formed in this tapered section. Less preferably, however, the vent hole 176 can be formed in the untapered portion 182 within the scope of the present invention.

Figure 19:
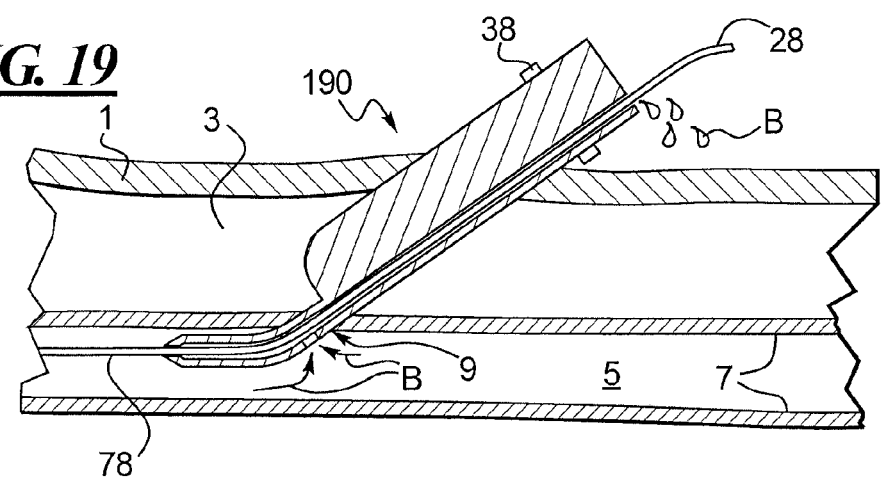
FIG. 19 diagrammatically illustrates a cross-sectional view of yet another embodiment in accordance with the present invention in one preferred use.

FIG. 19 illustrates yet another embodiment in accordance with the present invention. A depth marker 190 is similar to the delivery cannula 160 having the integral control tip 168, but does not include a lumen 166. A collar 38 is positioned on the outer surface of the depth marker, and permits the user to record the depth of the blood vessel 5 relative to the outer surface of the epidermis 1. The depth marker 190 is otherwise used in the same manner as the other embodiments of depth markers described herein.

Figure 20:
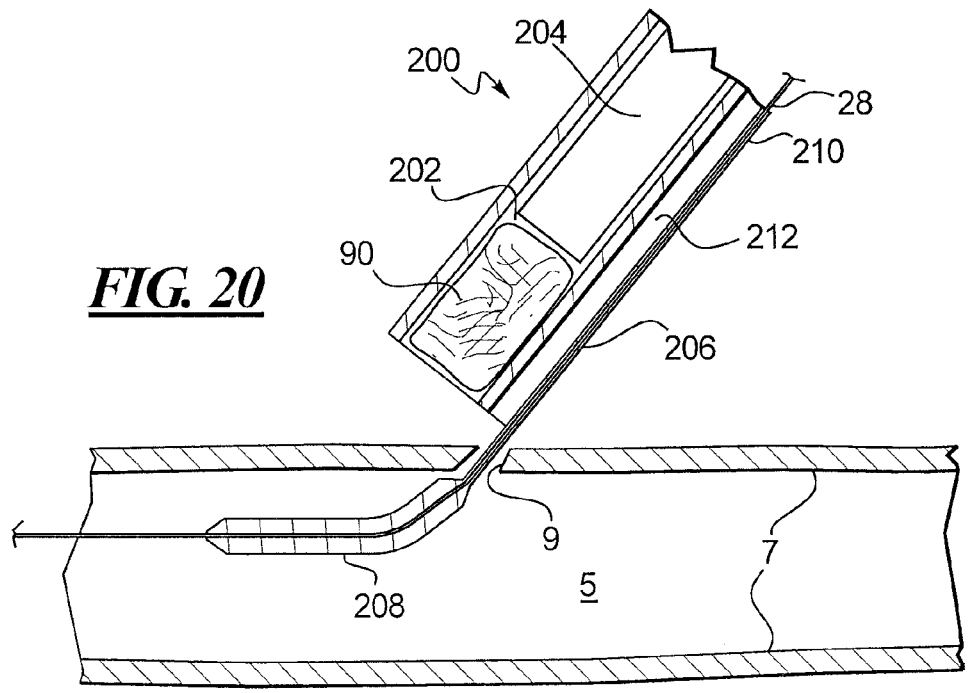
FIG. 20 diagrammatically illustrates a cross-sectional view of yet another embodiment in accordance with the present invention in one preferred use.

FIG. 20 illustrates yet another embodiment in accordance with the present invention. A biaxial delivery cannula 200 includes a lumen 202 sized to receive a pledget 90 and a pledget pusher or piston 204 which extends proximally out of the delivery cannula 200. The delivery cannula 200 also includes an integral control tip 206 having a longitudinally extending through lumen 210 extending from the control head 208 proximally to the proximal end of the delivery cannula in a manner similar to other embodiments described herein. The lumen 210 is sized to slidingly receive the wire 28, and preferably forms a seal with the wire 28 as also described elsewhere herein.

The delivery cannula 200 further includes a vent lumen 212 laterally offset from the lumen 202 and the lumen 210, and preferably between the lumenae 202, 210. In a fashion similar to that previously described herein, the vent lumen 212 permits blood to flash to the proximal end of the delivery cannula 200 to give a visual indication of when control of the puncture site 9 is made and lost.

Figure 21:
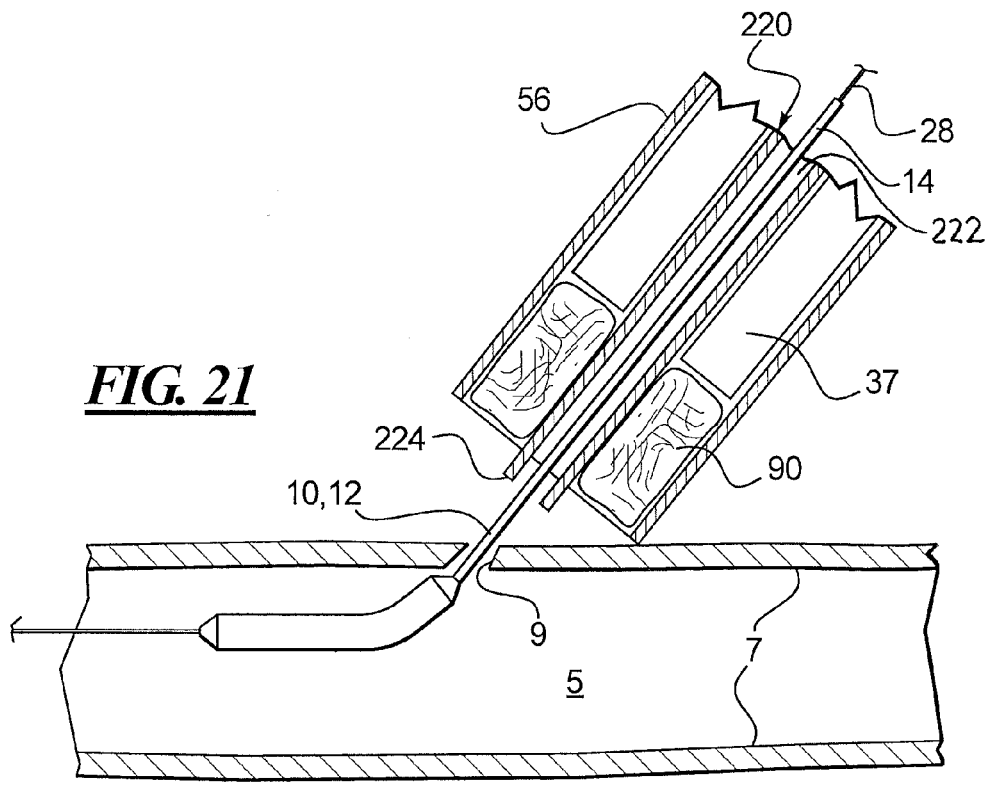
FIG. 21 diagrammatically illustrates a cross-sectional view of yet another embodiment in accordance with the present invention in one preferred use.

FIG. 21 illustrates yet another embodiment in accordance with the present invention. The embodiment illustrated in FIG. 21 is similar is some respects to the embodiment illustrated in FIG. 7. A delivery cannula 56, control tip 10 or 12, pledget 90, pusher 37, and wire 28 are similar or the same as described above, and are used in combination with a coaxial vent tube 220 which extends longitudinally through the pusher 37 and the pledget 90. The vent tube 220 includes a longitudinally extending lumen 222 which is sized to receive the control tip 10, 12 therein with an annular clearance to permit blood to flash proximally through the vent tube 220. Because the vent tube 220 performs the function of permitting blood flash, the shaft 14 of the control tip 10, 12 can be formed without a lumen 34, and can be dimensioned with a smaller outer diameter to increase the annular clearance between the shaft and the vent tube 220. The shaft 14 preferably maintains its relative flexibility to permit the tactile feedback previously described herein. The embodiment illustrated in FIG. 21 is used in a manner otherwise similar to those previously described herein.

Figure 22:
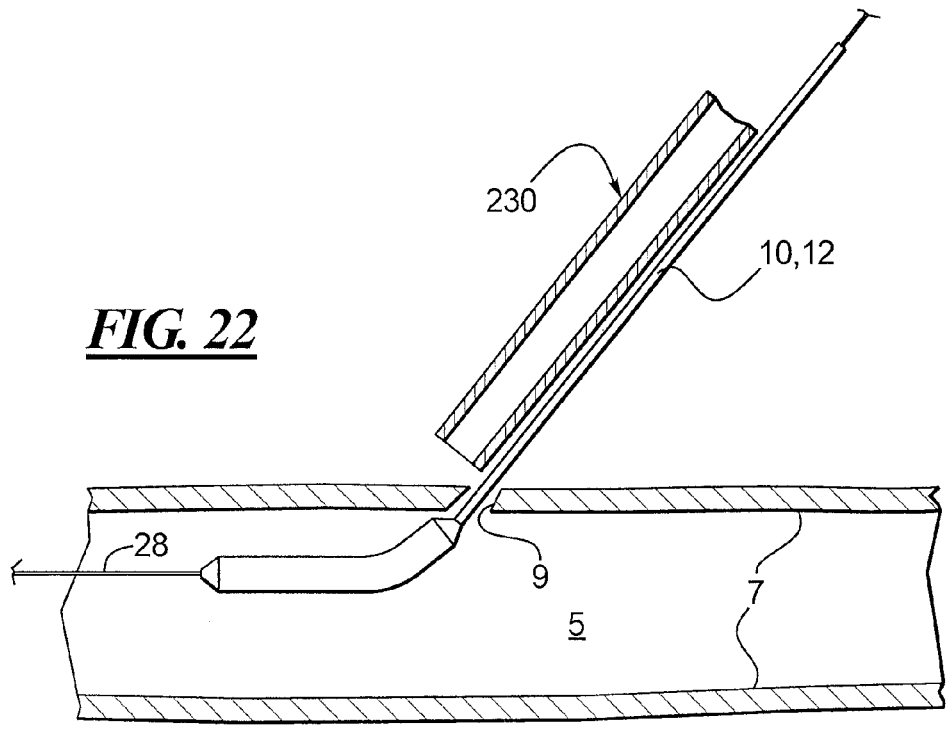
FIG. 22 diagrammatically illustrates a cross-sectional view of yet another embodiment in accordance with the present invention in one preferred use.

FIG. 22 illustrates yet another embodiment in accordance with the present invention. As illustrated in FIG. 22, a vent tube 230 can be used with a control tip 10, 12 so that the vent tube and control tip are advanced laterally next to each other to the puncture site 9. The vent tube 230 permits blood to flash proximally to give a visual indication of when control of the puncture site 9 is made and lost by the control head of the control tip.

For all of the embodiments of the control tip herein, the outer diameter of the central portion is between about 5 French and about 9 French, preferably between about 6 French and about 7 French. The length of the control head, between the distalmost end and the proximal end of the proximal tapered portion, is between about 1.5 inches (3.8 cm) and about 3 inches (7.6 cm), preferably between about 1.5 inches and about 2 inches (6.4 cm), and more preferably about 1.875 inches (4.8 cm). Control heads of these dimensions are well suited for controlling puncture sites as described herein, particularly puncture sites used during Seldinger-type vascular access.

The transverse cross sectional profile of all of the foregoing structures can be any desired shape, including square, oval, triangular, and preferably circular. The materials out of which the control tip, pledget pusher, and delivery cannula are constructed are preferably selected to be relatively rigid and biocompatible, and more preferably are biocompatible polymers, biocompatible metals and metal alloys, and combinations thereof.

While the invention has been described in detail with reference to preferred embodiments thereof, it will be apparent to one skilled in the art that various changes can be made, and equivalents employed, without departing from the scope of the invention. All of the aforementioned documents are incorporated by reference in each of their entireties herein.

What is claimed is:

1. An apparatus useful for inhibiting blood loss out a puncture site in a blood vessel wall and for indicating the location of a blood vessel comprising:
   a vent tube including a tubular shaft having a proximal end, a distal end, and a lumen extending longitudinally between the proximal end and the distal end; and
   a control head on the distal end of the vent tube shaft, the control head including a proximal end portion, a distal end portion having a distal port, and a central portion between the proximal end portion and the distal end portion, the control head including a lumen extending from the distal port to the vent tube shaft lumen, the control head further comprising a hole extending laterally through the control head and communicating the control head lumen with the exterior of the control head, wherein the control head proximal end portion is externally tapered.

2. An apparatus in accordance with claim 1, wherein the control head distal end portion is externally tapered.

3. An apparatus in accordance with claim 1, wherein the control head lumen has a substantially constant inner diameter.

4. An apparatus in accordance with claim 1, further comprising a tubular shaft positioned around the vent tube shaft, the tubular shaft including a proximal end, a distal end, and a lumen extending longitudinally between the tubular shaft proximal end and the tubular shaft distal end, the inner diameter of the tubular shaft lumen being larger than the outer diameter of the vent tube.

5. An apparatus in accordance with claim 4, wherein the tubular shaft is affixed to the vent tube so as to inhibit relative longitudinal motion of the tubular shaft and the vent tube.

6. An apparatus in accordance with claim 5, further comprising an elastic ring slidingly positioned on the exterior of the tubular shaft.

7. An apparatus in accordance with claim 4, wherein the vent tube is slidingly received in the tubular shaft lumen.

8. An apparatus in accordance with claim 4, wherein the tubular shaft further comprises a proximal fluid seal and a distal fluid seal between the vent tube and the tubular shaft.

9. An apparatus in accordance with claim 4, wherein the tubular shaft lumen at the distal end of the tubular shaft has an inner diameter that increases distally.

10. An apparatus in accordance with claim 1, further comprising a wire extending through the vent tube lumen, the wire having an outer diameter less than the vent tube lumen inner diameter.

11. A pledget delivery and blood vessel puncture site control system comprising:
    a control tip including:
    a vent tube having a tubular shaft with a proximal end, a distal end, and a lumen extending longitudinally between the proximal end and the distal end; and
    a control head on the distal end of the vent tube shaft, the control head including an externally tapered proximal end portion, a distal end portion having a distal port, and a central portion between the proximal end portion and the distal end portion, the control head including a lumen extending from the distal port to the vent tube shaft lumen;
    a pledget pusher positioned around the vent tube shaft, the pledget pusher including a tubular shaft having a proximal end, a distal end and a lumen extending longitudinally between the pledget pusher proximal end and the pledget pusher distal end, the inner diameter of the pledget pusher lumen being larger than the outer diameter of the vent tube; and
    a delivery cannula positioned around the pledget pusher, the delivery cannula including a tubular shaft having a proximal end, a distal end, and a lumen extending longitudinally between the delivery cannula proximal end and the delivery cannula distal end, the inner diameter of the delivery cannula lumen being larger than the outer diameter of the pledget pusher;
    the control head extending distally from the delivery cannula distal end, the delivery cannula distal end extending distally of the pledget pusher distal end.

12. A system in accordance with claim 11, wherein the control head is sized to be slidable through the delivery cannula lumen.

13. A system in accordance with claim 11, further comprising a pledget positioned in the delivery cannula lumen distal of the pledget pusher distal end.

14. A system in accordance with claim 11, further comprising a handle having a proximal end and a distal end, the handle and the control tip together further comprising a motion limiting device, portions of the motion limiting device being formed on the vent tube adjacent the vent tube proximal end, and portions of the motion limiting device being formed on the handle proximal end, the motion limiting device limiting longitudinal motion of the vent tube relative to the handle over a distance X.

15. A system in accordance with claim 14, wherein the control head extends distally from the delivery cannula distal end the distance X.

16. A system in accordance with claim 14, wherein the pledget pusher further comprises a proximal hub positioned in the handle, wherein the pledget pusher is slidable in the delivery cannula between a proximal position with the pledget pusher proximal hub engaging the vent tube portions of the motion limiting device, and a distal position with the pledget pusher proximal hub engaging the handle distal end.

17. A system in accordance with claim 11, further comprising a handle having a proximal end and a distal end, the handle including a distal hub, wherein the delivery cannula includes a proximal hub, the handle distal hub and the delivery cannula proximal hub including mating structures which releasably hold the handle and the delivery cannula together.

18. A system in accordance with claim 11, further comprising a handle having a proximal end, a distal end, at least one side extending between the handle proximal end and the handle distal end, and an open space adjacent to the at least one side, the pledget pusher including a proximal hub positioned in the handle open space.

19. A system in accordance with claim 18, wherein the pledget pusher is slidable in the delivery cannula between a proximal position and a distal position with the pledget pusher proximal hub engaging the handle distal end.

20. A system in accordance with claim 11, wherein the pledget pusher distal end includes a countersunk taper having a taper angle substantially the same as the taper angle of the control head externally tapered proximal end portion.

21. A system in accordance with claim 11, further comprising a pledget hydration device having a body with a proximal end, a distal end, an interior chamber, a tubular extension extending from the body distal end, a stop adjacent the tubular extension, and a proximal opening, the tubular extension sized to receive the delivery cannula therein, the stop sized and configured to prevent the delivery cannula from entering the interior chamber and sized and configured to permit the pledget pusher and control head to pass into the interior chamber.

22. A method of positioning a pledget adjacent to the exterior surface of a blood vessel puncture site in a patient, comprising the steps of:
    advancing a control head of a control tip through the puncture site and at least partially into the blood vessel, the control tip including a proximal portion extending out of the puncture site and out of the patient;
    advancing an assembly over the control tip proximal portion and adjacent to an exterior surface of the blood vessel, the assembly including a delivery cannula having a lumen, a pledget pusher in the delivery cannula, and a pledget in the delivery cannula;
    proximally retracting the control head, after the assembly advancing step, so that the control head is adjacent the pledget; and
    expelling the pledget from the delivery cannula,
    wherein the step of proximally retracting the control head comprises engaging the pledget with the control head.

23. A method in accordance with claim 22, wherein the step of proximally retracting the control head comprises engaging the blood vessel puncture with the control head.

24. A method in accordance with claim 22, wherein the steps of advancing the control head and advancing the assembly are performed simultaneously.

25. A method in accordance with claim 22, wherein the step of advancing the control head is performed before the step of advancing the assembly.

26. A method in accordance with claim 22, further comprising the step of:
    proximally retracting the delivery cannula and the control tip relative to the puncture site and relative to the pledget pusher.

27. A method in accordance with claim 26, further comprising the step of:
    proximally retracting the control tip relative to the puncture site and relative to the pledget pusher.

28. A method in accordance with claim 26, wherein the expelling step further comprises the step of distally advancing the pledget pusher to push the pledget out of the delivery cannula.

29. A method in accordance with claim 28, further comprising proximally retracting the control head and the pledget pusher relative to the delivery cannula, the control head being retracted through the pledget, the delivery cannula distal end engaging the pledget.

30. A method in accordance with claim 29, wherein the expelling step further comprises the step of distally advancing the pledget pusher to compress the pledget.

31. A method in accordance with claim 22, wherein the control tip includes a fluid flow path from the control head to the proximal end of the proximal portion, and further comprising stopping the step of advancing the control head after blood from the blood vessel has traveled along the fluid flow path to the control tip proximal end.

32. A method in accordance with claim 31, further comprising stopping the step of advancing the assembly after distal portions of the assembly bump into the blood vessel wall.

33. A method in accordance with claim 22, wherein the step of advancing the control tip and the step of advancing the assembly are performed simultaneously.

34. A method of measuring the distance between an epidermal outer surface and the outer surface of a blood vessel, the blood vessel having a puncture therethrough at a puncture site, comprising the steps of:
    advancing a control tip through subcutaneous tissue and into the blood vessel through the puncture;
    advancing a tubular shaft over the control tip until a distal end of the tubular shaft engages the outer surface of the blood vessel, wherein advancement of the tubular shaft is stopped when distal portions of the tubular shaft bump into the blood vessel wall and blood from the blood vessel flashes out a proximal end of the tubular shaft; and
    positioning a marker along the tubular shaft against the epidermal outer surface.

35. A method in accordance with claim 34, wherein the step of advancing the control tip and the step of advancing the tubular shaft are performed simultaneously.

36. A method in accordance with claim 34, wherein the step of advancing the control tip is performed before the step of advancing the tubular shaft.

37. A method in accordance with claim 34, wherein the step of advancing the control tip is stopped after blood from the blood vessel flashes out a proximal end of the control tip.

* * * * *

UNITED STATES PATENT AND TRADEMARK OFFICE
CERTIFICATE OF CORRECTION

PATENT NO. : 7,625,352 B1 Page 1 of 1
APPLICATION NO. : 09/621670
DATED : December 1, 2009
INVENTOR(S) : Ashby et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 759 days.

Signed and Sealed this

Twenty-sixth Day of October, 2010

David J. Kappos
*Director of the United States Patent and Trademark Office*